(12) United States Patent
Martin

(10) Patent No.: US 7,317,659 B2
(45) Date of Patent: Jan. 8, 2008

(54) MEASUREMENT OF AIR CHARACTERISTICS IN THE LOWER ATMOSPHERE

(75) Inventor: Andrew Louis Martin, Ferny Creek (AU)

(73) Assignee: Tele-IP Limited, Victoria (AU)

( * ) Notice: Subject to any disclaimer, the term of this patent is extended or adjusted under 35 U.S.C. 154(b) by 215 days.

(21) Appl. No.: 11/153,802

(22) Filed: Jun. 15, 2005

(65) Prior Publication Data

US 2005/0232082 A1    Oct. 20, 2005

Related U.S. Application Data

(63) Continuation-in-part of application No. 10/784,686, filed on Feb. 23, 2004, now abandoned, which is a continuation of application No. PCT/AU02/01129, filed on Aug. 19, 2002.

(30) Foreign Application Priority Data

Aug. 23, 2001 (AU) .................................... PR7203
Sep. 21, 2001 (AU) .................................... PR7832

(51) Int. Cl.
    *G01S 15/02* (2006.01)
(52) U.S. Cl. ..................... 367/89; 367/87; 73/861.25
(58) Field of Classification Search .................. 367/87, 367/89; 73/861.25
    See application file for complete search history.

(56) References Cited

U.S. PATENT DOCUMENTS

| | | |
|---|---|---|
| 2,507,121 A | 5/1950 | Silvian |
| 3,671,927 A | 6/1972 | Proudian et al. |
| 3,675,191 A | 7/1972 | McAllister |
| 3,889,533 A | 6/1975 | Balser |
| 4,558,594 A | 12/1985 | Balser et al. |
| 5,509,304 A | 4/1996 | Peterman et al. |
| 5,544,525 A | 8/1996 | Peterman et al. |
| 5,874,676 A | 2/1999 | Maki, Jr. |
| 6,040,898 A | 3/2000 | Mroski et al. |
| 6,087,981 A | 7/2000 | Normat et al. |
| 6,208,285 B1 | 3/2001 | Burkhardt |

OTHER PUBLICATIONS

Bradley, S. G., "Use of COded Waveforms for SODAR Systems," Meterol. Almos. Phys. 71, 15-23 (1999).*

* cited by examiner

*Primary Examiner*—Ian J. Lobo
(74) *Attorney, Agent, or Firm*—Hovey Williams LLP

(57) ABSTRACT

Sodar systems and methods for acoustically sounding air are disclosed in which chirps longer than 300 ms—and preferably with durations of tens of seconds—are used along with matched filter and/or Fourier processing methods to derive phase signals indicative of air characteristics in range. A listen-while-transmit strategy is preferred, the direct signal being removed by subtracting the phase signals from two or more receivers located near the transmitter so as to be in the same noise environment. The resultant differential signals can be related to cross-range wind with range distance. In one example, apparatus (100) is employed comprising a reflector dish (102) over which one central loudspeaker (110) and four microphones (112, 114, 130 and 132) are mounted, the microphones preferably being located on cardinal compass points and having their axes (124, 126) slightly angled with respect to the vertical transmission axis (122).

44 Claims, 16 Drawing Sheets

(h)

(i)

(A)

(C)

(E)

Derivation of Temperature From Phase Inputs

MEASUREMENT OF AIR CHARACTERISTICS IN THE LOWER ATMOSPHERE

RELATED APPLICATION

This application is a continuation-in-part of application Ser. No. 10/784,686 filed Feb. 23, 2004 now abandoned, which is a continuation of International Application Serial No. PCT/AU02/01129 filed 19 Aug. 2002, published under PCT Article 21(2) in English, and claiming priority from Australian patent applications PR 7203 filed 23 Aug. 2001 and PR 7832 filed 21 Sep. 2001, and applicant claims the benefit of Australian patent applications PR 7203 filed 23 Aug. 2001 and PR 7832 filed 21 Sep. 2001, the disclosures of application Ser. No. 10/784,686, International Application Serial No. PCT/AU02/01129, and Australian patent applications PR 7203 and PR 7832 are hereby incorporated by reference.

TECHNICAL FIELD

This invention relates to the use of acoustic signals for atmospheric sounding and is particularly concerned with sodar techniques for measuring air velocity variation—such as horizontal wind speed variation, wind-shear and/or turbulence—in the lower atmosphere. The invention may, however, be applied to measuring local density variation in the atmosphere, such as may be caused by temperature gradients, temperature, thermal inversions and variations in moisture content.

The apparatus and methods of the intention are also applicable to wind profiling in the vicinity of airports to enhance air safety and/or permit higher density air traffic at airports.

The atmospheric sounding techniques of the invention belong to a class of technology recently dubbed SODAR, or SOund Direction and Ranging. Sodar is to be distinguished from sounding techniques using electromagnetic waves, such as RADAR (RAdio Direction and Ranging), LIDAR (LIght Direction and Ranging), AERI (Atmospheric Emittance Radiance Interferometry) and the hybrid RASS (Radio Acousitc Sounding Systems) in the atmosphere. However, common to all these techniques in their current form is a concern with Doppler signals and the use of Fourier transform methods in processing such signals. While SONAR (Sound Navigation and Ranging) has not been mentioned because it is employed in liquid media, some overlap between the exclusively acoustic techniques of sonar and sodar may be seen because sonar ranging and imaging methods have been applied in air—as in some camera ranging, non-destructive testing and medical imaging systems.

BACKGROUND OF THE INVENTION

Though exclusively acoustic methods for wind profiling and the like have a long history, Coulter & Kallistratova in their 1999 article "The Role Acoustic Sounding in a High-Technology Era" [Meteorol. Atmos. Phys. 71, 3-19] show that these methods have not lived up to their promise. This appears to have been largely due to an inability to achieve an adequate signal-to-noise ratio [s/n].

Sodars for atmospheric sounding have almost universally employ short (millisecond), single-tone high power pulses, multiple receivers and simple timing circuits to determine the sequence of echoes at different receivers needed to deduce the height of various discontinuities in the atmosphere. U.S. Pat. No. 2,507,121 to Sivian [1950] disclosed a method for measuring the height of atmospheric discontinuities that involved sending such a pulse vertically into the atmosphere and, after cessation of the transmitted pulse, detecting vertically returned echoes using two similar receivers located near the transmitter. In the embodiment of most interest, the first receiver is shielded against receiving echoes but the second is not and the two receivers are connected so that their outputs are opposed and the net signal can be displayed on an oscilloscope. In the event of a normally returned echo, a pip is displayed because only the second receiver detects a signal. However, in the event of local noise such as a gunshot both receivers detect the same signal and no pip is displayed.

U.S. Pat. No. 3,889,533 to Balser [1973] disclosed an 'acoustic wind sensor' in which an acoustic transmitter illuminates a cylindrical column of air by either CW (continuous wave) or pulsed signals and remote receivers are pointed at narrow or broad portions of two or more sides of the side column to detect acoustic energy scattered laterally therefrom. The Doppler components of this scattered energy are then extracted to determine wind velocity at the various heights. In order to observe a portion of the illuminated column, which is—say—1000 m from the ground, the receivers need to be spaced from the transmitter by a roughly similar distance. Also, significant spacing is needed to sufficiently attenuate the direct signal [sometimes called the 'zero Doppler' signal] from the transmitter. An application of this system to the detection of persistent vortices near runways was disclosed in U.S. Pat. No. 3,671,927 to Proudian and Balser.

U.S. Pat. No. 3,675,191 to McAllister [1972] disclosed the use of four adjacent arrays of acoustic transducers capable of being used as speakers and microphones, the arrays being aligned with the cardinal points of the compass and being shielded from one another, except at their upper faces. Short acoustic pulses were transmitted vertically upwards and the relative timing of the returned echoes at each of the four arrays gave the height and bearing of wind layers. [It might be noted that the physics of acoustic sounding was well documented in 1969 by McAllister and others in "Acoustic Sounding—A New Approach to the Study of Atmospheric Structure" in Proc. IEEE Vol. 57, 579-587.] U.S. Pat. No. 4,558,594 to Balser disclosed the use of an acoustic phased array capable of directing successive pulses in different directions, the echoes from one pulse being detected by the array before the next is transmitted. U.S. Pat. No. 5,521,883 to Fage et al uses a similar phased array to send pulses of different frequencies in different directions and then listen for all echoes simultaneously, thereby decreasing the cycle time. The typical angle of elevation for pulse transmission in the latter systems was between 20 and 30 degrees. The relatively low elevation angle is to enhance Doppler components in the returned echoes due to horizontal (rather than vertical) wind speed in the direction of interrogation.

In recent years, radar DSP (digital signal processing) techniques have been applied to the sodar to achieve improved s/n. In particular, pulse-compression techniques have been used, in which the echoes from a phase or frequency coded pulse are processed with matched filters using Fourier transforms to give the range resolution normally associated with a shorter pulse with a much higher peak power. Such coded pulses are said to have 'pulse-compression' waveforms or to be 'pulse coded'. For simplicity, pulses of this type will be called 'chirps'. In an article entitled: "Use of Coded Waveforms for SODAR Systems" [Meteorol. Atomos. Phys. 71, 15-23 (1999)], S G Bradley recently reviewed, with simulations, the use of radar pulse compression techniques to improve amplitude discrimination in sodar. Examples of the use of pulse compression techniques in radar can be found in U.S. Pat. No. 6,208,285 to Burkhardt, U.S. Pat. No. 6,087,981 to Normat et al, and U.S. Pat. No. 6,040,898 to Mroski et al. Despite the application of such sophisticated techniques to sodar, a review by Crescenti entitled, "The Degradation of Doppler Sodar Performance Due to Noise" [Crescenti, G. H., 1998, Atmospheric Environment, 32, 1499-1509], found that severe problems remain even at modest ranges of 1500 m.

OUTLINE OF THE INVENTION

From one aspect, the invention comprises methods and apparatus for acoustic sounding in air in which echoes from a transmitted chirp (along with extraneous acoustic inputs) are detected during transmission of the chirp. In other words, there is 'listening while sending'.

This avoids the need to limit pulse length to secure near-range capability, which is essential in known pulsed sodars that employ the 'transmit then listen' strategy. For example, if the pulse length of a conventional sodar is one second, the first 170 m of range will be lost because the receiver will be turned off for the first second; a 10 s pulse will lose the first 1700 m of range. Typically, therefore, pulsed sodars of the art employ pulses of a few tens of milliseconds. By contrast, our chirps are of at least 300 ms duration and, preferably longer than 10 s; indeed, we have used chirps of up to 50 s, the duration only being limited by our current signal processing capacity. Preferably, the duration of the chirp is at least 5% of the listening time; that is, there is at least 5% overlap between chirp transmission and echo reception, but it will be appreciated that listening time depends on the distance range covered. For ranges up to a few km, we prefer chirp lengths well over 50% of receive time. As a convenient guide, we listen for about 6 s longer than the chirp for each km of range. Thus, in a system with a 1 km range, the chirp/pulse duration might be 15 s and the listening time 21 s; for a 2 km range, we might use a 31 s chirp and listen for 43 s. Generally, we start listening at the commencement of the chirp transmission to obtain data from ground level up. For some applications however we may not want the ground level data and choose to start listening some time after the end of the chirp transmission.

The longer the chirp, the higher its energy for a given transmitter power and the better the echoes can be discriminated using appropriate matched filter and/or Fourier techniques. It is thus much easier to detect faint echoes behind the direct signal from the transmitter with long, low power chirps than with conventional short high-power pulses. The danger of receiver overload is also mitigated by the use of modern microphones that have a large dynamic range. Of course, acoustic shielding of the receiver(s) from the direct transmitter signal is sensible.

Indeed, the improvement now possible with the use of long chirps and matched filter techniques is such that, from another aspect, the invention comprises methods and apparatus for acoustic sounding in air in which the echoes from a chirp of greater than 300 ms are detected and processed using matched filter and Fourier techniques. Either the 'send then listen' or the 'listen while sending' strategy may be used. As already noted, chirps with duration in the order of seconds are preferred; with chirp durations of tens of seconds being favored in may situations.

From another aspect, the invention comprises methods and apparatus in which multiple receivers are located near a common transmitter so that each will receive echoes from each transmitted chirp. Preferably, the receivers are located close enough to share a common acoustic and system noise environment and, preferably, they are arranged so as to receive the same direct signal (in both frequency spectrum and amplitude). This allows received signal components (eg, direct signal, ground clutter and noise) that are common to more than one receiver to be to be efficiently removed by differencing the signals from two or more receiver locations. Of course, by 'multi-receiver' we mean to include the situation where a single receiver is moved to multiple receiver locations and where a separate chirp is transmitted for each receiver location.

While the removal of the common unwanted direct signal, as well as common noise components and ground clutter, is highly desirable, it is very difficult to be done directly on the received signals for a chirp that lasts tens of seconds. According to another aspect of the invention we employ multiple acoustic receivers with a single transmitter and process the received acoustic signals in the (Fourier) frequency domain using matched filter techniques to generate a cumulative phase output for each receiver signal and then manipulate these outputs to achieve the appropriate measurement. Subtraction or differencing of the cumulative phase signals eliminates the direct signal, common noise, common ground clutter and the common signals due to variation in vertical wind speed, the residual differential cumulative phase then represents the variation of wind speed with range distance. This overcomes a major problem with conventional sodars, which cannot discriminate between returned Doppler signals due to vertical wind speed without a direct measurement and those due to horizontal wind speed.

However, comparison or differencing of two or more cumulative phase signals requires a common starting or reference point in the signals. This is conveniently the start of chirp transmission, which can be determined by the start of the received direct chirp or by an electronic signal from the transmitter. However, many other methods of synchronizing the receiver signals are possible. Thus, while it is desirable that the receivers are located in a common acoustic environment in the vicinity of the transmitter, it is not essential that they by equidistant from the transmitter in order to ensure that the direct chirp arrives at each receiver at the same time.

By transmitting two differently coded chirps (at the same time, using two transmitters or one after the other using one transmitter) the cumulative phase outputs can be manipulated to remove all common signals, and components due to cross-range wind, to allow generation of a further output that is indicative of variation of the speed of sound with range and, thus, variation of temperature with range. Preferably, the two chirps are identical positive and negative linear phase chirps (eg, the positive one rising from 800 to 1600 Hz and the negative one descending from 1600 to 800 Hz at the same phase rate.

Thus, the last mentioned aspect of the invention provides a further large improvement in s/n, allowing much improved echo discrimination with respect to the art, despite listening while sending. Also, simultaneous echo reception and processing by multiple receivers greatly improves cycle time.

A convenient arrangement of receivers in a system for vertical atmospheric sounding is to locate one receiver at each cardinal compass point around the transmitter and to slightly incline opposed receivers toward or away from one another. Thus, the phase components common to the N-S receiver signals are removed by phase differencing to leave that associated with variation of the net N-S wind over range distance. Systems of this type are suitable for vertical sounding in noisy environments such as airports, power stations and urban areas.

It will be appreciated that the invention is not limited to the use of four receivers, or to vertical sounding systems or to the symmetrical placement of receivers around a transmitter. The receivers may be arranged in a line, for example across a runway glide path with one or more transmitters to detect persistent vortices caused by the passage of large aircraft. The high-speed localized winds which can make up such vortices are difficult to quantify because the high Doppler shifts of echoes generated have considerable ambiguity. In this situation, another aspect of the invention involves the repeated analysis of recorded echo signals for each range point using a matched filter that is fed with a succession of different reference chirps so that, for each range point, a reference chirp is found that generates a zero phase gradient output (in the Fourier domain). That reference chirp is then indicative of the wind speed at that range point. It is also useful here (as well as in other applications envisaged by the invention) to take 'readings' in the absence of vortices to record ambient wind and noise conditions and to subtract the associated phase signals from those generated when there is a vortex present.

Whilst listening during sending is not essential for the implementation of the last described aspects of the invention, it is certainly desirable because it enables the use of long chirps, better echo discrimination and the effective elimination of range dead-zones.

The transmitted acoustic chirp can be generated by feeding a commercially available loudspeaker (transmitting acoustic transducer) with an electrical input signal from the sound card of a computer (for example), while the echoes can be detected using commercially available microphones (receiving acoustic transducers). The loudspeaker and microphone(s) can be mounted with separate concentrating reflectors (plates, horns, dishes or the like) or they may be mounted with a common reflector. For example, four microphones can be arranged in quadrature around a single loudspeaker above a single reflector dish so that the transmission axis is substantially axial with respect to the dish. Since the microphones are then offset with respect to the axis of the dish, the receiving axes of opposed pairs will be oppositely inclined toward the transmission axis; that is, each receiver will be most sensitive to echoes coming from a direction opposite to its location on the dish with respect to the transmission axis.

An arrangement where a loudspeaker and multiple microphones are mounted on a common structure allows the transmission axis to be conveniently aimed or set as desired by moving the structure. A system with a transmission axis of low elevation can be used, for example, to detect or characterize vortices caused by large aircraft landing or taking off at an airport. It is even possible to use airborne systems of this type to warn pilots of clear air turbulence (CAT) that is difficult to detect using radar. For example, a compact transmitter and receiver system could be mounted in the nosecone of a large aircraft. Alternatively, only the transmitter need be mounted in the nosecone since the receivers can be mounted in a row along the leading edge of the wings.

As already noted, the receiving axis of a receiver may be inclined with respect to the transmission axis and that, where multiple receivers and signal differencing are used, it is desirable that the axes of opposed receivers are equally inclined. The optimum angle of inclination will depend upon the aperture of the receivers, the range of the system and the desirability of locating the receivers in a common acoustic environment. An angle of 20 degrees in a system with a 3 km range is likely to place the receivers too far from one another to have a common acoustic environment, but this may not be so in a system with a range of only 250 m. Angles of inclination of between about 2 and 10 degrees have been found suitable, with angles between 4 and 7 degrees preferred. It will be seen that the point of intersection of a receiver axis with the transmission axis is not intended to be the nominal range of the sodar system. Indeed, highly satisfactory results have been obtained where medium aperture microphones are located about 1 m from the loudspeaker in a common dish with their receiving axes angled at about 4 degrees to the transmission axis. In effect, the receivers of an opposed pair are looking for wind-induced Doppler signals from large illuminated areas on opposite sides of the transmission axis but in the same plane as the receiving axes and the transmission axis.

As already noted, it is desirable (but not necessary) to space multiple receivers equidistant from and near to a common transmitter so that each will be subject to the same ambient noise (as well as other common components). Generally, the louder and less uniform the noise environment, the nearer the receivers need to be to one another to ensure that each is subjected to the same environmental noise, as far as practicable. We have found that, in a noisy environment, the distance between a receiver and the transmitter should be of the order of metres. In a quiet environment, it can be of the order of 10 m.

In general, the transmitted chirp should have a tonal range (acoustical bandwidth) suited to the object being sounded. We have found that wind-shear below 3000 m is best sounded at the lower end of the audible range; for example, 500-5000 Hz, more preferably between 800 Hz and 3 kHz and most preferably between 1.0 kHz and 2.5 kHz.

While the tones in a chirp can be modulated in frequency and/or phase in many ways in conformity with pulse compression techniques, we have found it convenient to use a linear chirp in which the frequency increases or decreases smoothly and linearly from start to finish of the chirp. Ideally, such a chirp has a uniform rate of phase-shift. The use of positive and negative linear chirps is of particular value in the reduction of unwanted phase components in techniques for measuring air temperature disclosed herein. Linear chirps are also easily generated and their echoes convenient to process using available DSP and Fourier techniques implemented using personal computers.

Although (as already noted) long duration chirps offer the potential of high system processing gains (lower s/n), long chirps also result in significant computational demands when using the high signal sampling rates and the Fourier techniques needed to achieve such gains. We have found that current readily available FFT algorithms, DSP chips and PCs set a practical limit on chirp duration of about 40-50 s at sampling rates of about 96 k Hz. This typically represents some 1400 samples per m, given a range of 3000 m. Indeed, the computational demands are such that we prefer to dedicate one PC to each receiver of a multi-receiver system so that echo analysis for all receiver signals can proceed in parallel to the point where signal differencing takes place. In the future, developments in chips, FFT/matched filter techniques and PCs may allow longer chirps to be processed using a single PC—or, much faster updating times using the pulse lengths presently achievable.

DESCRIPTION OF EXAMPLES

Having portrayed the nature of the present invention, particular examples will now be described with reference to the accompanying drawings. However, those skilled in the art will appreciate that many variations and modifications can be made to the chosen examples while conforming to the scope of the invention as outlined above.

SUMMARY OF DRAWINGS

In the accompanying drawings:

FIG. 5 is a block diagram illustrating a system for extracting east-west phase information from the echoes received by the east and west microphones of the chosen system example.

Figure 1:
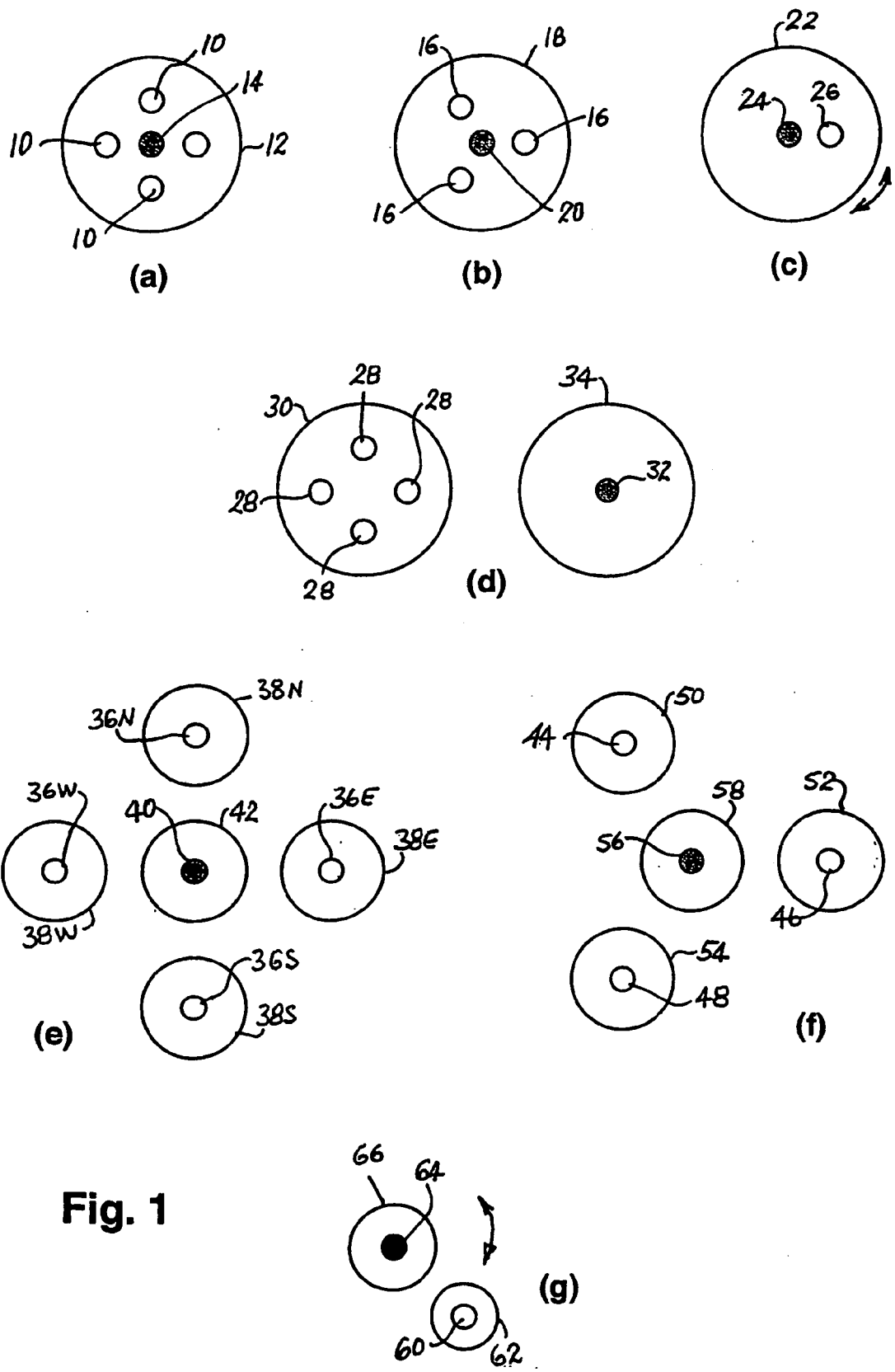
FIG. 1 is a series of diagrammatic plan views showing selected arrangements of transmitters and receivers, the transmitters (loudspeakers) being shown as small shaded circles and the receivers (microphones) being shown as small unshaded circles.
Figure 1:
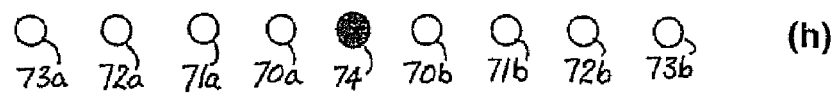
Figure 1:
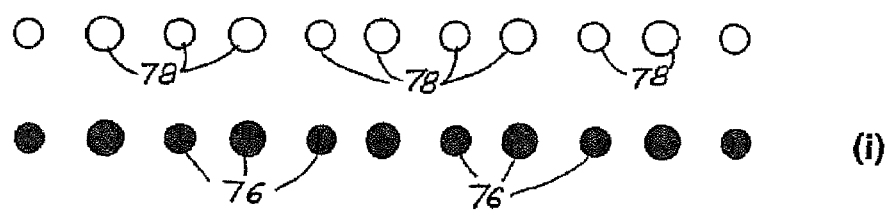

As illustrated by the simple plan-view diagrams (a) to (i) of FIG. 1, there are many possible ways in which the transmitter and receivers of sodar systems envisaged by this invention can be configured, and many others are possible.

Diagram (a) shows a convenient and economical configuration in which four microphones 10 are spaced within and around a common parabolic reflector dish 12 and a single loudspeaker 14 is located at the central focus of dish 12. In this way, the amplitude lobe of the transmitted pulse is vertical but the amplitude lobe each received echo is angled slightly to towards the axis of dish 12 and loudspeaker 14.

Diagram (b) of FIG. 1 shows three microphones 16 evenly spaced in a common dish 18 that also has a centrally located loudspeaker 20. Diagram (c) shows a dish 22 with a central loudspeaker 24 and only one offset microphone 26, dish 22 being mounted so that it can be rotated to successively put microphone 24 in different positions [eg, those illustrated in (a) or (b)]. Diagram (d) shows four microphones 28 mounted in a common receiving dish 30 that is separate and spaced from the associated loudspeaker 32, which is mounted in its own transmission dish 34. Optionally, receiving dish 30 may have more or less than four microphones located therein. Diagram (e) illustrates a configuration in which each of four microphones 36N, 36S, 36E and 36W has its own receiving dish 38N, 38S, 38E and 38W (respectively) and a single loudspeaker 40 has its separate dish 42. Diagram (f) is similar to (e) except only three microphones 44, 46 and 48 and their respective dishes 50, 52 and 54 are deployed around a single microphone 56 and its dish 58. Finally diagram (g) shows a configuration in which a single microphone 60 and its dish 62 are mounted so as to be rotatable around a single loudspeaker 64 and its dish 66, so as to be able to simulate configurations such as those of (e) and (f).

FIG. 1(h) is a plan view of a linear array of four pairs of receivers 70a and 70b, 71a and 71b, 72a and 72b, and, 73a and 73b arranged in a row with one receiver of each pair positioned on either side of a single transmitter 74. Transmitter 74 generates a narrow spherically propagated beam orthogonal to the line of receivers so that the signals received by each receiver pair can be processed to remove the direct signal and common noise. In the linear array of FIG. 1(i), which is also shown in plan view, A row of transmitters 76 is arranged parallel to a row of receivers 78, a common signal being fed to all transmitters so as to generate a linearly propagated sound wave. The arrangements of FIGS. 1h) and 1(i) are suited for arrangement across the glide path of an airport to detect persistent vortices. [A system of this nature will be described in more detail below.]

Figure 2:
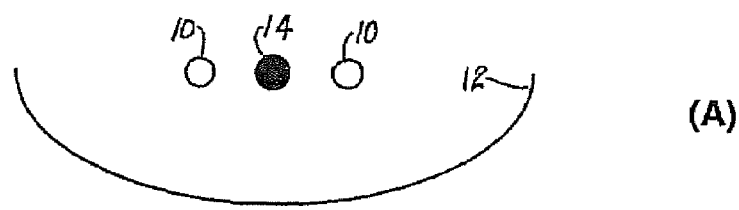
FIG. 2 is a series of diagrammatic elevations showing co-located and separately located transmitter and receiver arrangements.
Figure 2:
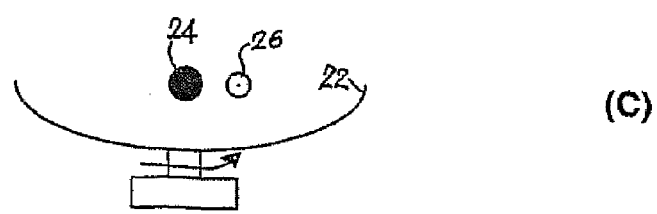
Figure 2:

The diagrams (A), (C) and (E) of FIG. 2 are diagrammatic elevations of configurations (a), (c) and (e) respectively of FIG. 1.

Figure 3:
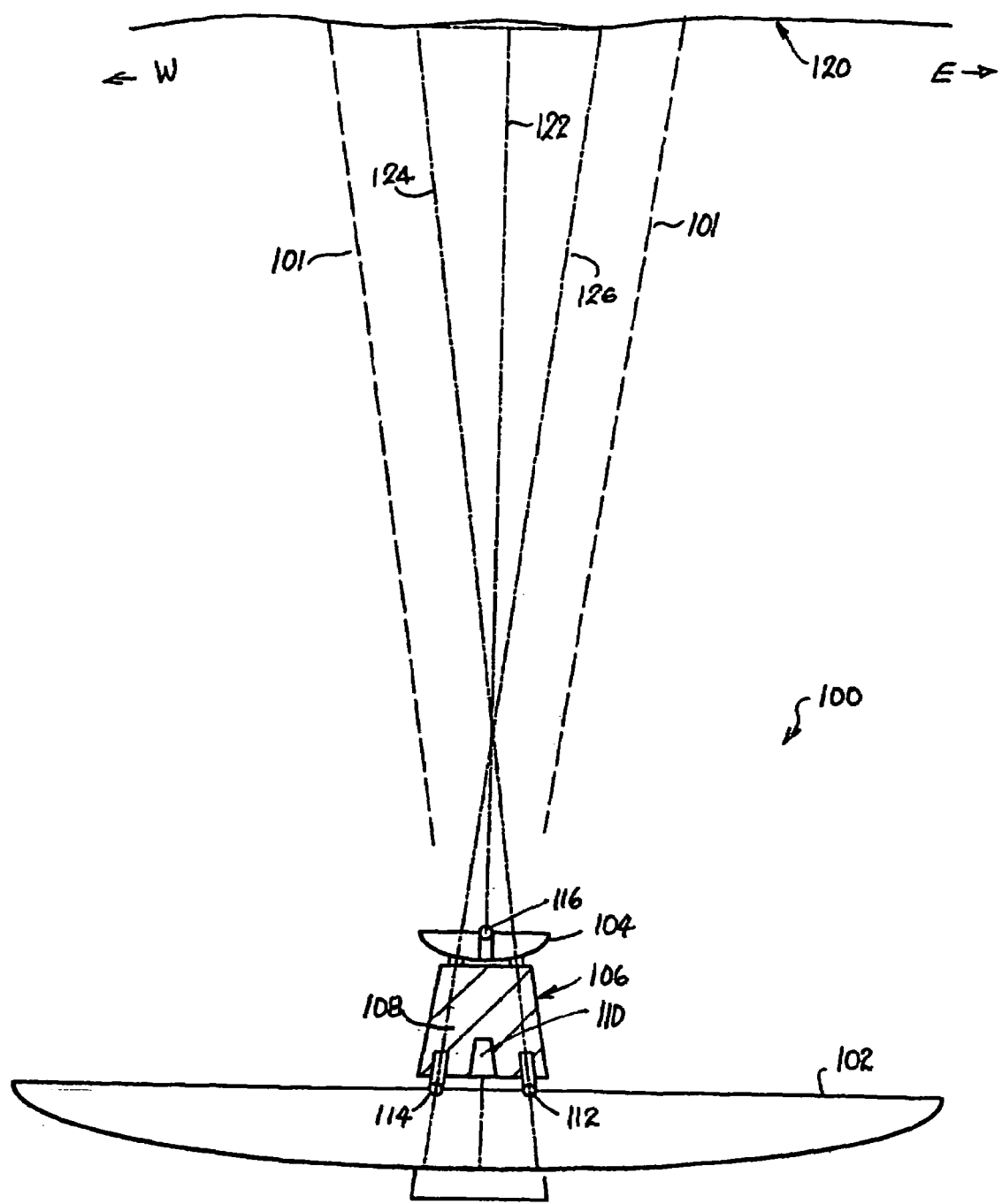
FIG. 3 is a diagrammatic sectional elevation showing the arrangement of the transmitter and receivers of the first system example.

The system 100 of the first example, illustrated in FIG. 3, approximates the arrangement of FIG. 1(a) and FIG. 2(A) and is adapted for vertical or inclined atmospheric sounding where both cross-range (horizontal, in this case) and along-range (vertical, in this case) wind velocities are required. For convenience, however, it will be assumed that chirps from the transmitter are directed vertically upwards to illuminate an inverted cone of air indicated at 101 by broken lines. Also for convenience, the cardinal points of the compass will be referred to as N, S, E & W, as well as north, south, east and west where thought necessary.

System 100 includes a large main dish 102 and a small secondary dish 104 mounted directly above the main dish. A transmitter/receiver module 106 is supported centrally above large dish 102 (by struts that are not shown) and, in turn, supports small dish 104 on the top thereof. Module 106 comprises a sound-adsorbent molding 108, into the bottom of which a central loudspeaker 110 and four peripheral microphones are fitted.

The microphones are arranged in quadrature and aligned with the cardinal points of the compass so that, in the sectional diagram of FIG. 3, the W microphone is shown at 112 (on the east/right side of loudspeaker 110) and the E microphone is shown at 114 (on the west/left side of loudspeaker 110). This apparent reversal of naming the E and W microphones is convenient because the microphone on the west side of the loudspeaker is positioned to be most sensitive to echoes coming from the east, after reflection and focusing by dish 104, and vise versa. The axis of each microphone is angled to the vertical at between about 3 and 10 degrees. The loudspeaker 110 and microphones 112 and 114 are located near the focus of large dish 102. A fifth directional microphone 116 is located at the focus of small dish 104.

In the diagram of FIG. 3, a single horizontal reflective atmospheric discontinuity (such as the nocturnal boundary layer or other thermal inversion layer—TIL), 120 is shown. Since loudspeaker 110 is pointed vertically downward, it will generate a downwardly directed vertical beam that will be reflected vertically upward by large dish 102 along a central system axis 122. Some echoes will be returned down axis 122 to microphone 116 on small dish 104. However, the beam of interrogating pulses will be conical and will illuminate a significant area of the TIL 120 around axis 122 and echoes will be returned from an area to the west of axis 122 along the axis 124 of west microphone 112 and be most strongly detected by that microphone (in comparison with the signals detected by the other microphones). Similarly, echoes from TIL 120 to the east of axis 122 will travel along the axis 126 and be most strongly received by east microphone 114.

While echoes returned from TIL 120 and detected by W microphone 112 may be centered about path 124, microphone 112 will pickup echoes from a large area of TIL 120 in the vicinity of axis 122. Thus echoes from a source near axis 122 are likely to be picked up by all microphones. Doppler (phase) components common to echoes detected by all microphones at much the same time are therefore indicative of the vertical velocity of TIL 120 in the vicinity of axis 122, and it can be expected that these common components will be most prominent in the echoes detected by central microphone 116. If the Doppler components of echoes received by W and E microphones 112 and 114 are subtracted, the common Doppler (phase) components indicative of the vertical velocity component will be removed and it can be assumed that the remaining Doppler (phase) components are due to net wind speed in the east/west direction. Similar subtraction of the Doppler components of echoes received by the N and S microphones will yield the net wind speed in the north/south direction.

In practice, of course, there will be many atmospheric discontinuities at many altitudes within range that generate echoes and that the time of return of such echoes will be indicative of range or altitude and the amplitude of the echoes will be indicative of the magnitude of the respective discontinuities.

The generation of chirps for transmission and the processing of received echoes may be implemented in many ways, whether in software or hardware. The mode of implementation will be influenced by the desired chirp length, listening time/intended range, sampling rates, and up-date frequency, since these factors largely determine computation demand. To provide desired high processing gain, chirp durations greater than 0.3 s are considered essential, with durations of tens of seconds desirable. Prior art pulsed systems using the transmit-then-listen strategy typically have transmit times in the order of tens of milliseconds and a net listening time of about 6 s for a range of 1000 m. By contrast, in the present example, for a range of 1000 m and net listening time of 6 s, the selected chirp duration is 37 s and the total listening time is 43 s. For the same total transmitted energy the chirp of the present example can have a thousand-fold lower peak power than a 37 ms chirp typical of the prior art. The total listening time of the present example is more than seven times that typical of the art for a 1000 m range, providing much greater opportunity for processing gain. By using chirps (pulse-compression waveforms) and matched filter processing, processing gains are further multiplied many-fold.

Figure 4:
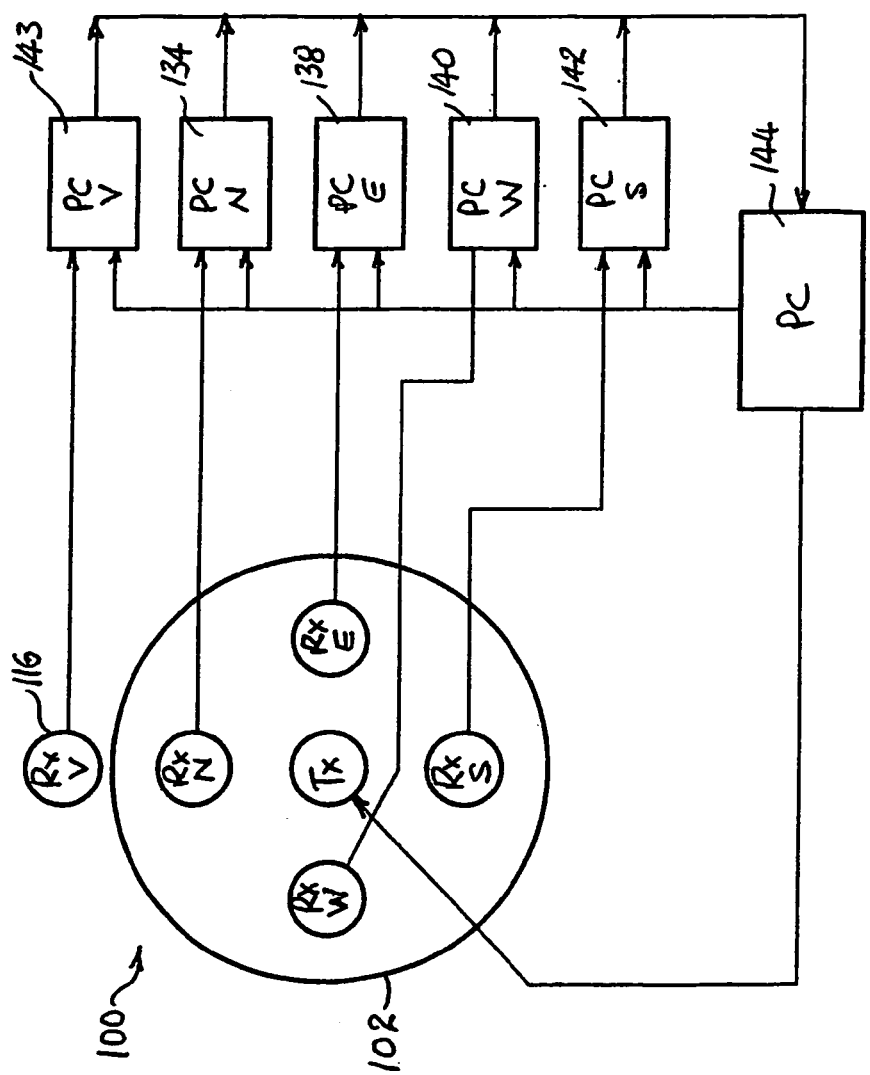
FIG. 4 is a schematic plan of the system of FIG. 3 showing the general manner in which signals to the transmitter are generated and signals from the receivers are processed.

The computation demands of the system of the example are, however, substantial and, in this case, were thought to justify dedicating a PC to process the signals from each receiver and using another PC as a controller. FIG. 4 shows this arrangement in which the N and S receiver microphones are shown at 130 and 132 respectively, the dedicated N, E, W & S and vertical (V) calculating PCs are shown at 134, 136, 138, 140, 142 and 143 respectively and the controller PC is shown at 144. Controller PC 144 generates the chirp for transmission by transmitter/loudspeaker 110 and the reference chirp for use in matched filtering by the calculating PCs. It also collects the results of the computations of PCs 134-142 for integration, display and reporting.

In this example, the chirp has a phase/frequency that increases linearly over the 37 s from 800 Hz to 1600 Hz (the chirp could just as easily decrease linearly from 1600 Hz to 800 Hz) and is emitted at an acoustic power of a few hundred milli-Watts that remains constant for the duration of the chirp. This type of pulse compression waveform has a small bandwidth (about 800 Hz) and is simple to generate accurately using a PC sound card and conventional loudspeaker driver circuits for powers up to many Watts. It is also one for which a 'matched filter' or correlator can be readily designed and used to extract echoes of the chirp from received signals having high noise levels and to effectively compress the energy of each echo into a period of time that is much shorter than that of the transmitted chirp. The use of pulse-compression waveforms and matched filters thus yield very high processing gains.

Measurement of Cross-Range Wind Velocity

Figure 5A:
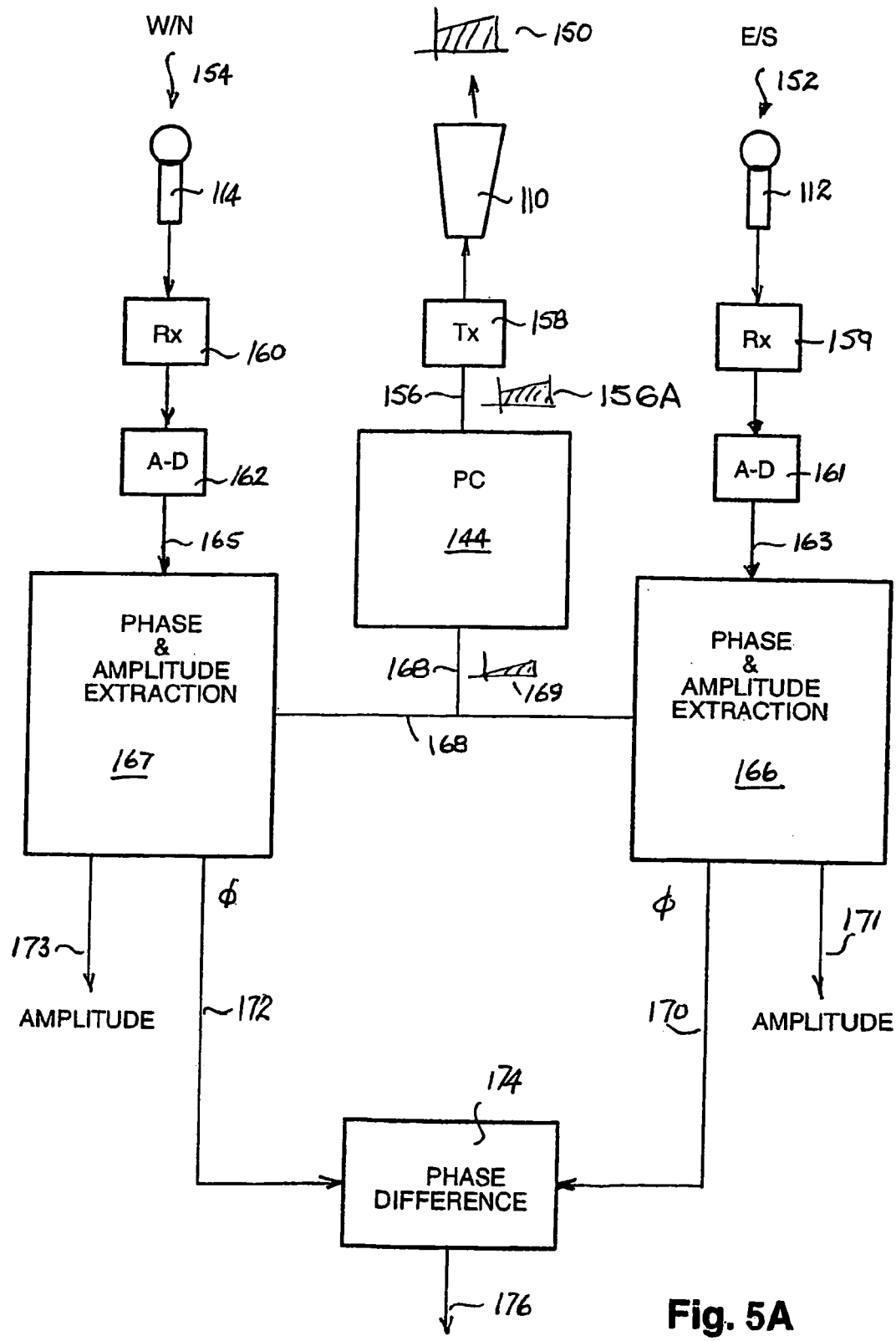
FIGS. 5A, 5B and 5C are block diagrams illustrating respective parts of a circuit and process by which windspeed, wind-bearing and wind-shear information with respect to height can be generated with the system of the first example.

System 100 of the chosen example is well suited for measuring various characteristics of horizontal (cross-range) wind. The manner in which the net phase difference between the east and west echoes is effected to derive the E-W wind speed with range distance will now be described with reference to FIGS. 5A, 5B and 5C. It should be appreciated that the system of FIG. 5A is duplicated for the extraction of the net phase difference between the north and south echoes in exactly the same manner. This is indicated by "W/N" and "E/S" in FIG. 5A. However, the following description will refer principally to the processing of the E & W echoes.

Figure 5B:
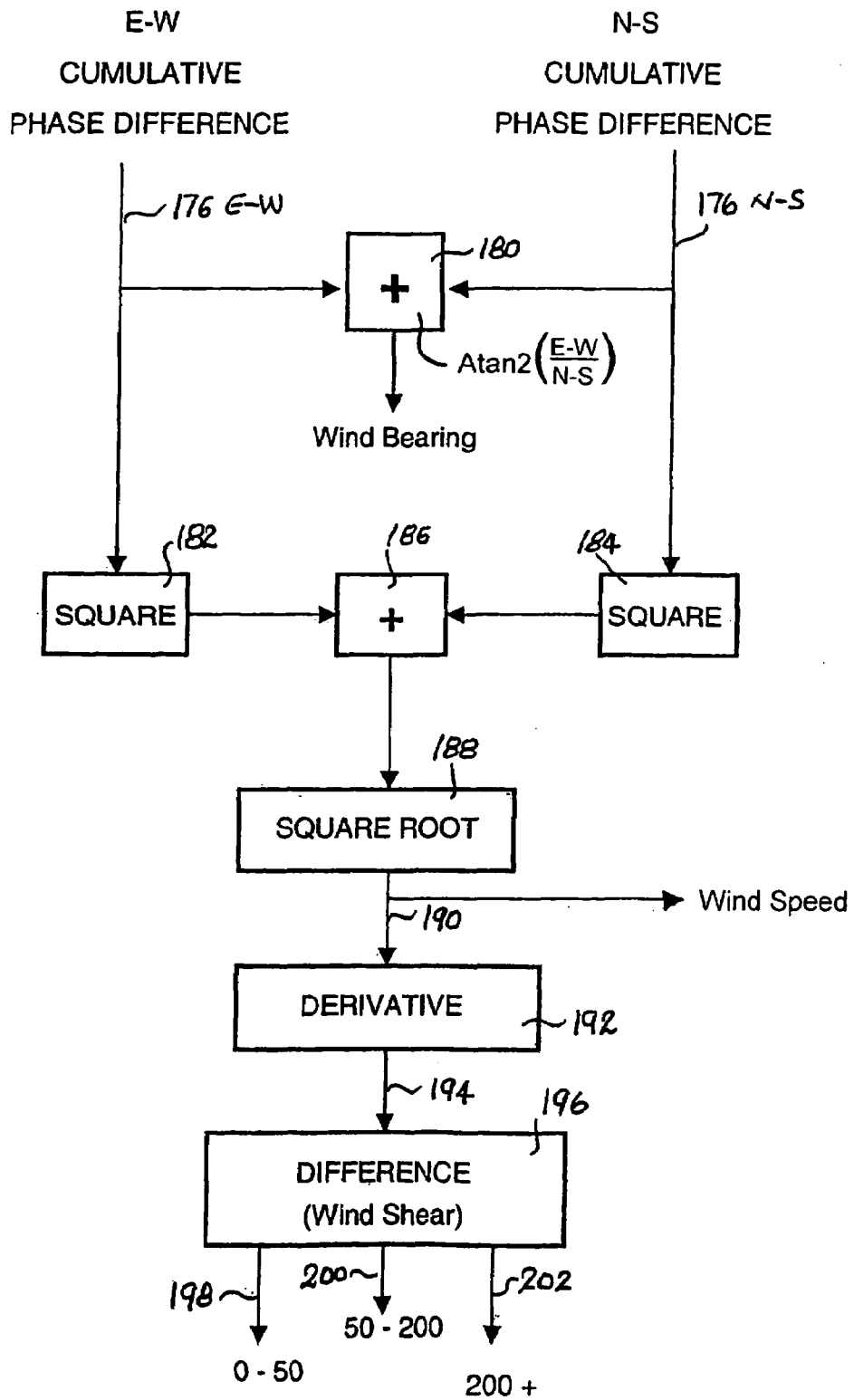
Figure 5C:
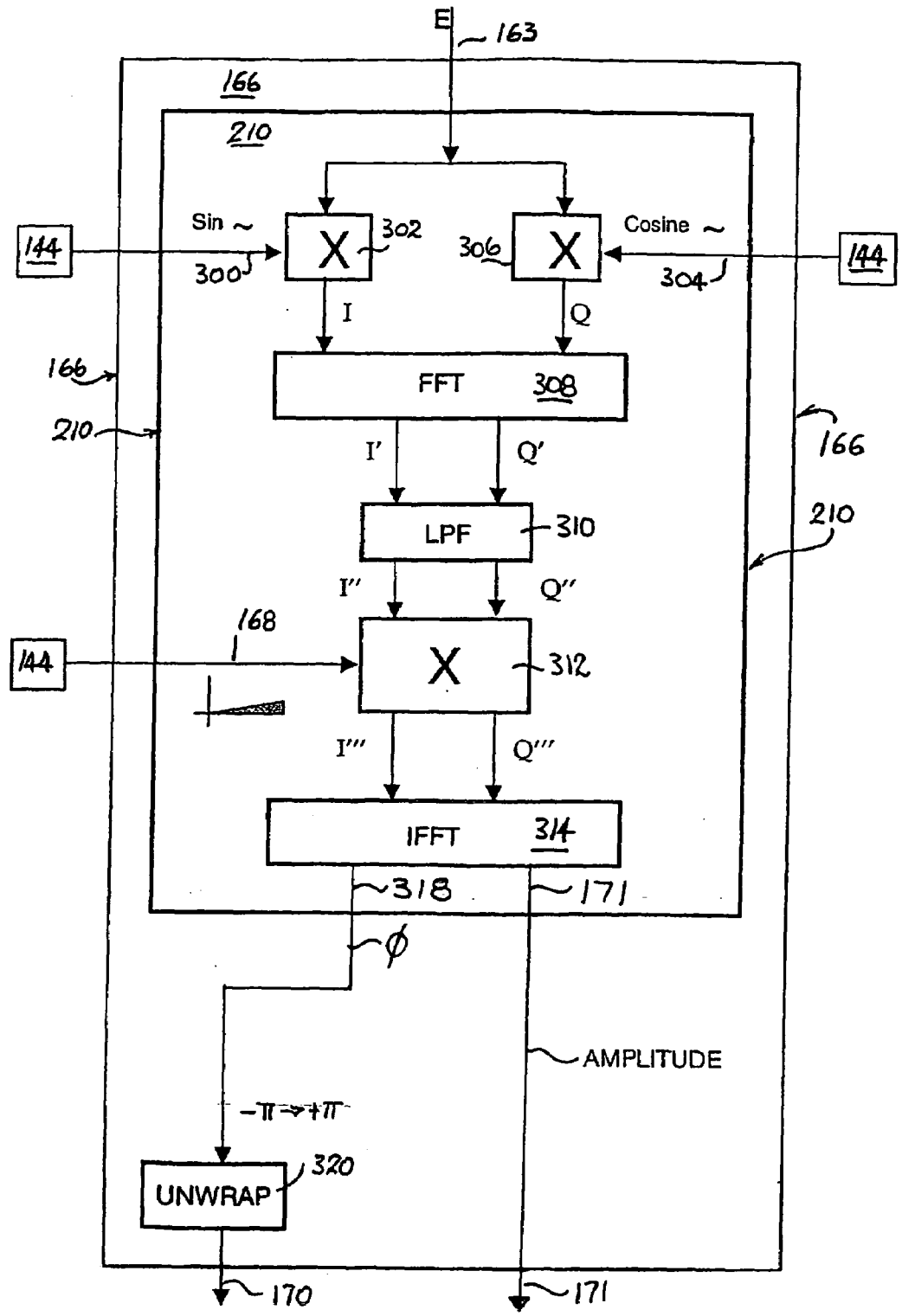

The processes of FIG. 5A are performed in dedicated E & W PCs 138 and 140 and control PC 144 to (i) extract the cumulative phase and amplitude information from the noisy received signal using matched filtering and (ii) difference the E-W cumulative phase information to eliminate the zero Doppler signal (and other common noise components) to yield a Doppler phase signals indicative of net east-west wind speed. The cumulative phase information and the differenced E-W and N-S phase information are illustrated graphically in FIG. 8. The E-W and N-S signals are then used as inputs for the circuit and process of FIG. 5B, from which overall wind velocity and wind shear information is derived. PCs 138 and 140 again do the processing, the results being collated and displayed on control PC 144 and illustrated graphically in FIG. 9. FIG. 5C illustrates in more detail the phase and amplitude extraction circuit, which includes a matched filter or correlator, shown in FIG. 5A. The phase extractor is substantially identical for each receiver and is implemented in the respective receiver PC. The circuit and process of FIG. 5 are illustrated and described generally because the techniques employed are analogous to known signal processing techniques used in radar.

In FIG. 5A, loudspeaker 110 is shown pointing upwards, the transmitted chirp is indicated by shaded graph 150, east microphone 112 is shown pointing up on the right side of the diagram to receive input signals indicated by arrow 152 and west microphone 114 is shown pointing up on the left side of the diagram to receive input signals indicated by arrow 154. Chirp 150 is generated using a control PC output 156 (indicated by associated graph 156A) to drive a transmitter circuit 158, which in turn, powers matched loudspeaker 110 to ensure that the acoustic power of transmitted chirp 150 is uniform over its whole bandwidth (about 800 Hz). In this example, the power is about 0.5 Watt; not enough to cause annoyance even in urban areas.

Figure 6:
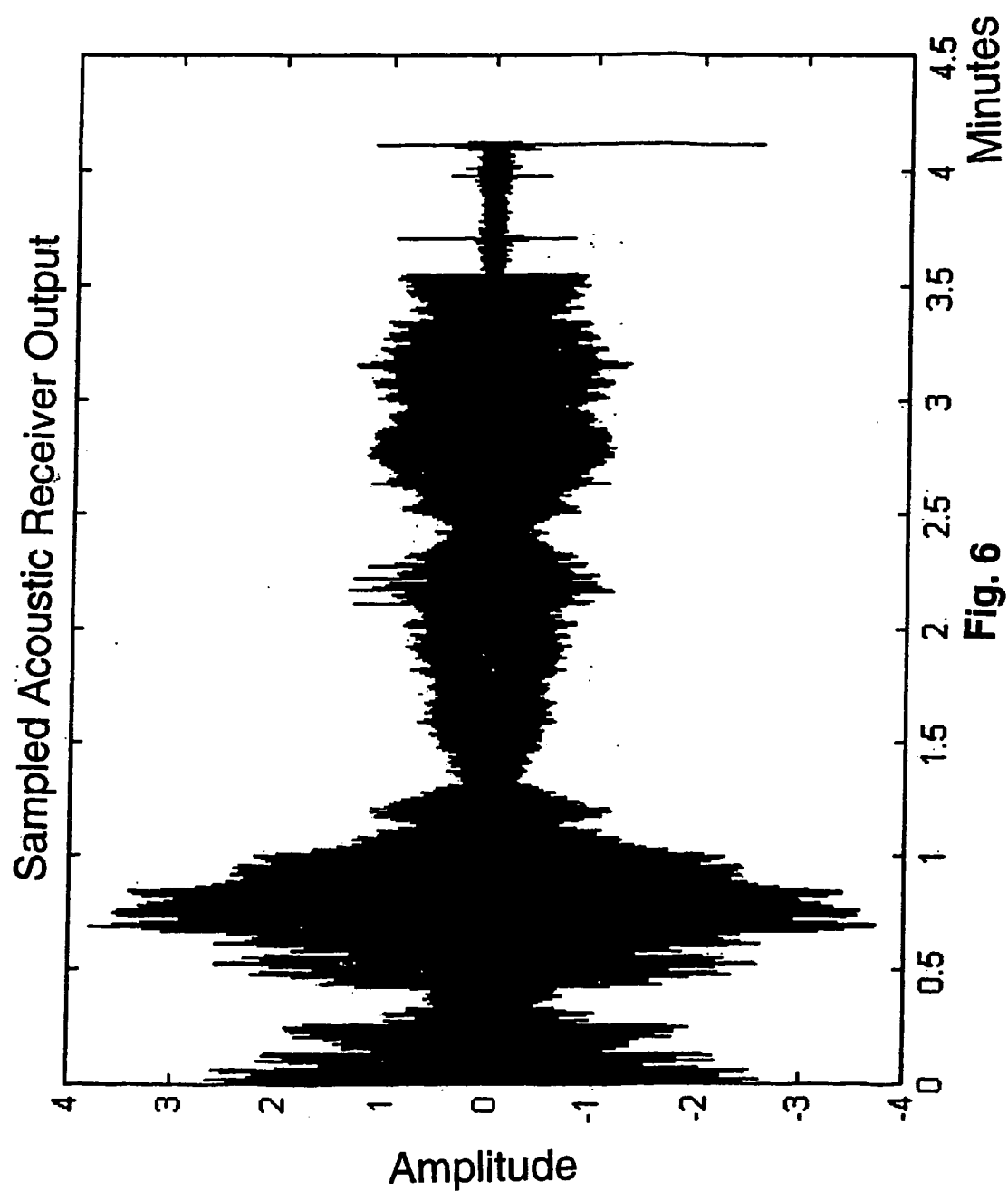
FIG. 6 is a histogram depicting a typical digitized acoustic signal detected by a receiver of the system of the first example.

Received east and west signals 152 and 154 are respectively processed (essentially amplified and band-pass filtered) in receivers 159 and 160, the outputs of which are sampled at 96 k/s and digitized by analog-digital (A-D) circuits 161 and 162 to generate digital receiver signals 163 and 165. A representation of signal 163 or 165 is shown in FIG. 6.

Outputs 163 and 165 are fed to phase and amplitude extraction circuits 166 and 167 that employ matched filters to correlate signals 163 and 165 in the Fourier domain with a version of the transmitted chirp, extract or derive echo phase and amplitude information therefrom. Said version of the transmitted chirp is provided via line 168 by control PC 144 to each extractor 166/167 and comprises the transmitted chirp shifted down by 800 Hz; ie, converted to a 0-800 Hz chirp as indicated in nearby graph 169. It may also be desirable to delay signal on line 168 with respect to the actual transmitted signal so as to select a desired range band of the system.

Extractor circuits 166 and 167 each have two outputs. Outputs 170 and 171 of extractor 166 are respectively indicative of the cumulative phase and amplitude of the input 163 after matched filtering (Fourier processing), the east cumulative phase being shown in FIG. 8(i), the south cumulative phase being shown in FIG. 8(v) and the east and south magnitudes being shown in the barchart of FIG. 9(i). Outputs 172 and 173 of extractor 167 are respectively indicative of the cumulative phase and amplitude of the input 165 after matched filtering, the west cumulative phase being shown in FIG. 8(ii), the north cumulative phase being shown in FIG. 8(iv) and the west and north amplitudes being shown in the barchart of FIG. 9(i). Cumulative phase outputs 170 and 172 contain the information from which wind velocity, direction and wind shear can be derived, as well as common phase noise and zero-Doppler components due to the direct signal and ground clutter. Cumulative phase outputs 170 and 172 are differenced in circuit 174 to remove the common components and output on line 176 as the net E-W phase or cumulative phase of graph (iii) of FIG. 8.

These outputs contain the information from which the E-W velocity and wind shear are derived.

Figure 8:
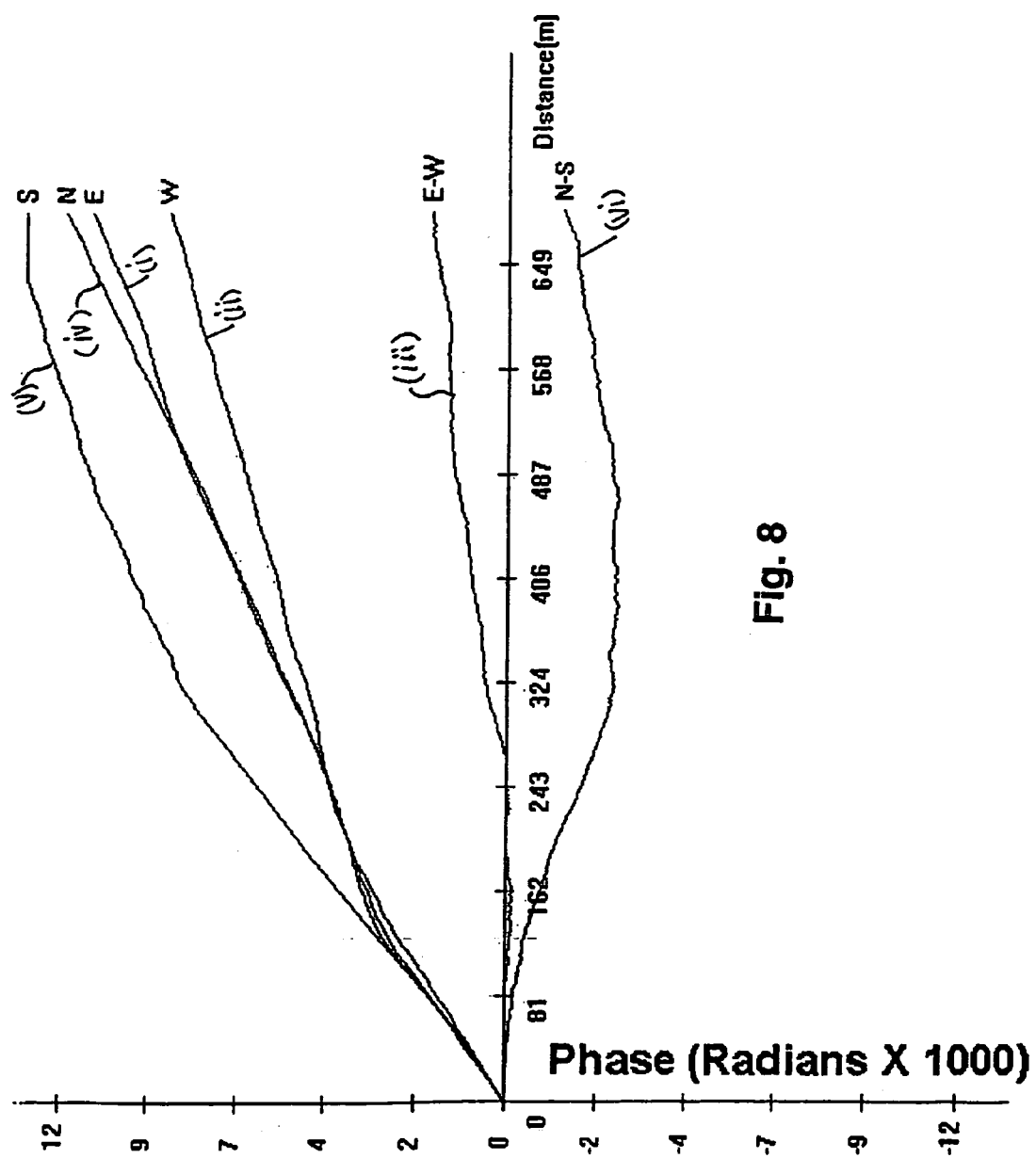
FIG. 8 is a series of graphs depicting the cumulative phase information derived from all receivers of the system of the first example.

As already noted, the circuit and process of FIG. 5 is applied in an identical manner to the north and south signals to derive the cumulative north phase illustrated graphically by FIG. 8(iv), the cumulative south phase illustrated by FIG. 8(v) and the net north-south phase variation with height illustrated by FIG. 8(vi). For convenience, east-west phase difference output from circuit will be identified as 176 E-W of and the north-south phase difference will be identified as 176 N-S.

Figure 9:
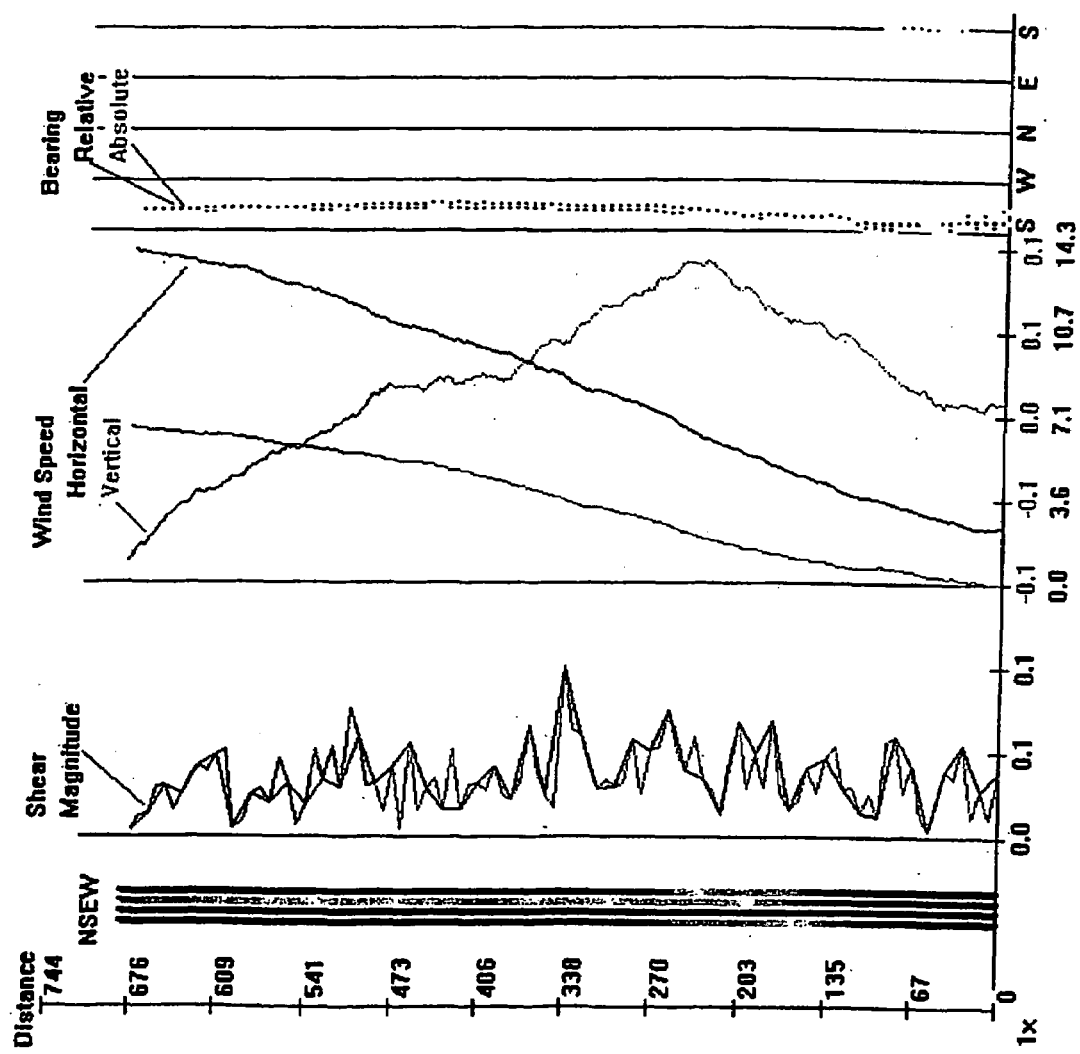
FIG. 9 includes bar charts and graphs showing the atmospheric wind characteristics output from the system of the first example.

FIG. 5B illustrates how outputs 176 E-W and 176 N-S are processed in the chosen example to generate wind speed and bearing (ie, wind velocity) and wind shear magnitude with range distance (altitude, in this case). Outputs 176 E-W and 176 N-S are fed to a combiner circuit 180 implementing the function A tan 2

$$\left(\frac{E-W}{N-S}\right)$$

from which wind bearing or direction is derived, as shown in FIG. 9(ii). This is done by determining whether the E-W signal is positive or negative and whether the N-S signal is positive or negative in order to place the wind direction in the correct quadrant of the compass. Thus, a positive E-W phase and a positive N-S phase will indicate that the wind direction is in the first quadrant, and so on. The angle in the first quadrant can be determined by computing the relevant vector to give a more precise indication of bearing.

By employing the well known square-root of the sum of the squares algorithm, the magnitude of the phase signal can be determined to output the wind speed and wind shear magnitudes. This is done by feeding outputs 176 E-W and 176 N-S to respective squaring circuits 182 and 184, summing the outputs of these circuits in adder 186 and deriving the square root in circuit 188. The resultant output on line 190 is indicative of the variation of wind speed with respect to altitude. This is illustrated by FIG. 9(iii).

By taking the derivative of the signal on line 190 using differentiator circuit 192 the magnitude of wind shear with altitude is output on line 194. FIG. 9(iv) illustrates this. Signal on line 194 can be further processed to apportion the wind shear into various magnitude bins using a differencing circuit 196 to generate a series of outputs 198-202 etc, which are illustrated by the graphs of FIG. 9(v).

Referring now to FIG. 5C, the basic operation of each extractor will now be described. Since the extractors are substantially identical, only extractor 166 for the east receiver will be described. Again it will be appreciated that the matched filter and the phase and amplitude extraction techniques adopted here are known to those skilled in the radar art. Preferably, as also mentioned before, each extractor is implemented in a separate PC that is dedicated to one receiver.

Figure 7A:
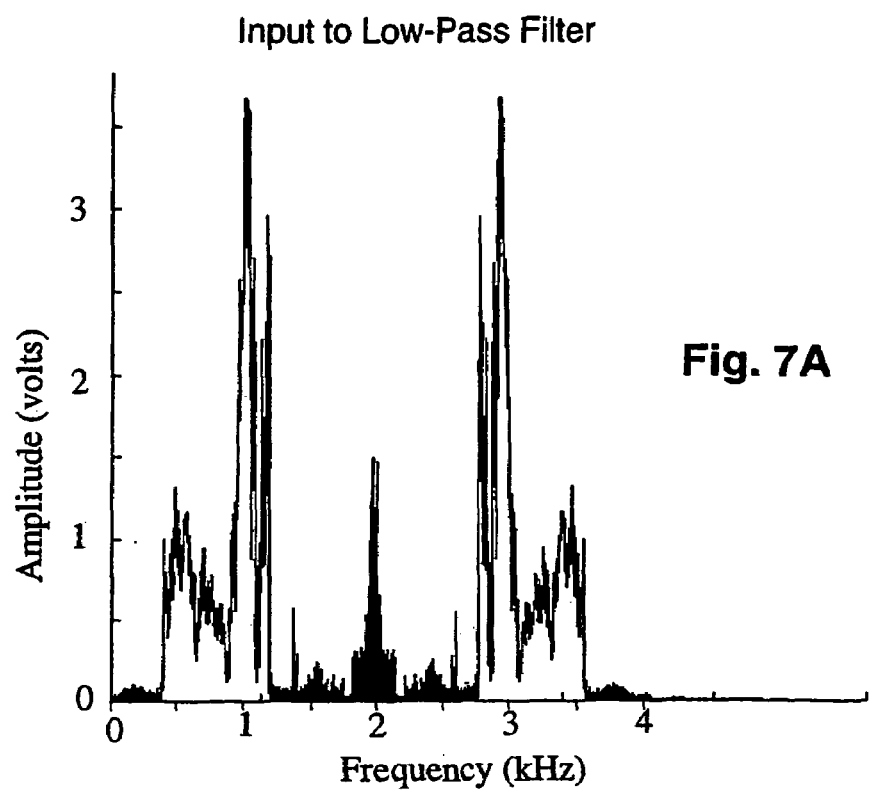
FIGS. 7A and 7B are graphs of typical signals before and after the low-pass filter of the matched filter of the system of the first example.
Figure 7B:
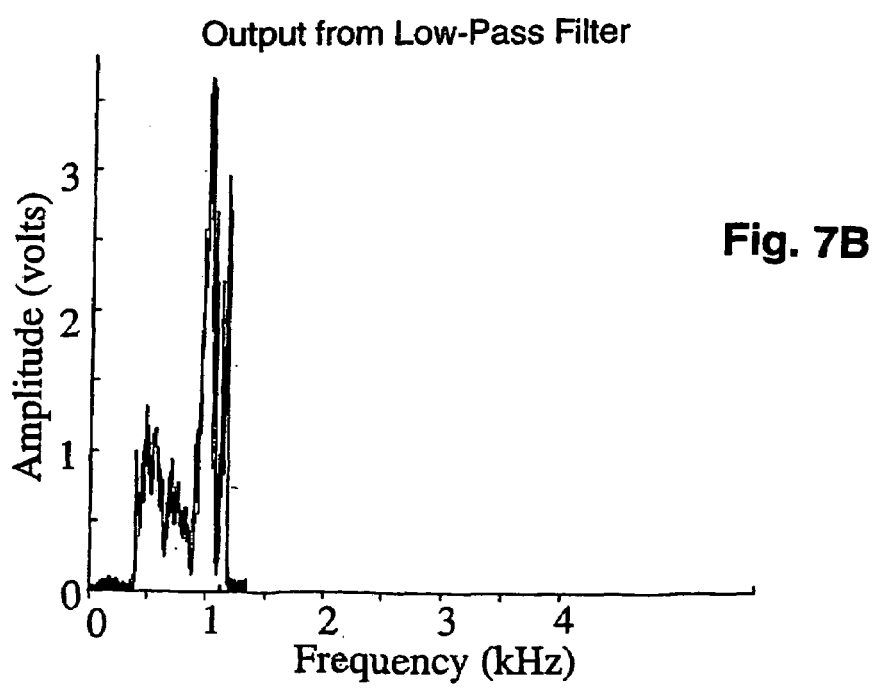

Extractor 166 essentially comprises a matched filter 210 that—in the Fourier or frequency domain—matches a reference chirp (usually a version of the transmitted chirp) to the confused time-domain echoes that are included in input signal 163. Each digitized sample of E input 163 is converted to complex form. The imaginary part (I) is generated by mixing the input with a digitized 2000 Hz sine signal 300 supplied by control PC 144 using multiplier 302, and the real part (Q) is generated by mixing the input with a digitized 2000 cosine signal 304 (also supplied by PC 144) using multiplier 306. The resultant I and Q signals for every sample taken during the listening period are fed to a complex FFT [fast Fourier transform] process 308, where all samples are presented and processed as an array to generate the frequency domain outputs I' and Q'. These outputs are low-pass filtered at 310 to remove the upper side band. FIGS. 7A and 7B show the unfiltered and filtered signal components Q' and Q", respectively. The filtered signals I" and Q" are then passed to complex multiplier 312 in which they are multiplied with the down-converted output signal 168 from the control PC 144. The result of this multiplication generates real and imaginary sample like outputs I''' and Q''' in the frequency domain and is then subjected to complex inverse FFT at 314 to generate phase and amplitude outputs 318 and 171 in the time domain.

Output 318 from IFFT 314 is then processed to provide corresponding phase output 170. Phase output 318 yields a succession of phase values between $-\pi$ and $+\pi$, which is input into an unwrap process 320. The unwrap process is known and implementations are available in programs such as MatLab. Essentially, process 320 counts the number of $2\pi$ phase shifts to generate an accumulated phase. For every transition from $+\pi$ to $-\pi$ (an increasing phase) the phase accumulator is increased by 1, and vice versa. This output can then be displayed as a radian count with respect to sample number (proxy for time and distance) and displayed graphically as in FIG. 8. The barchart (i) of FIG. 9 shows the variation of amplitude with height, each amplitude reading being color-coded to indicate magnitude. It will be appreciated that a sharp variation in processed signal amplitude at a given height is indicative of moisture or temperature change and not of wind shear. However, significant temperature differentials in the atmosphere will be accompanied by wind change.

Measurement of Air Temperature

Using the system of the above example, the variation of air temperature over range distance can be estimated by the use of positive and negative chirps and manipulating the cumulative phase outputs generated. This comprises the second detailed example of the application of this invention.

Though not essential, the use of substantially identical positive and negative linear chirps is highly desirable in the means for the measurement of temperature. Consistent with the above example, a positive chirp that rises in frequency from 800 to 1600 Hz and a negative chirp that falls in frequency from 1600 to 800 Hz over a period of 37 s will be assumed. It will also be assumed that the positive chirp is transmitted first and that the negative chirp is transmitted immediately after the listening time of 43 s has elapsed, there also being a listening time of 43 s after the negative chirp has been transmitted. In this case, it will be convenient to separately digitize the acoustic signals from each of the four receivers (N, S, E & W) for the positive chirp and for the negative chirp and to then process each in the manner describe above to extract the respective cumulative phase signal.

Figure 10:
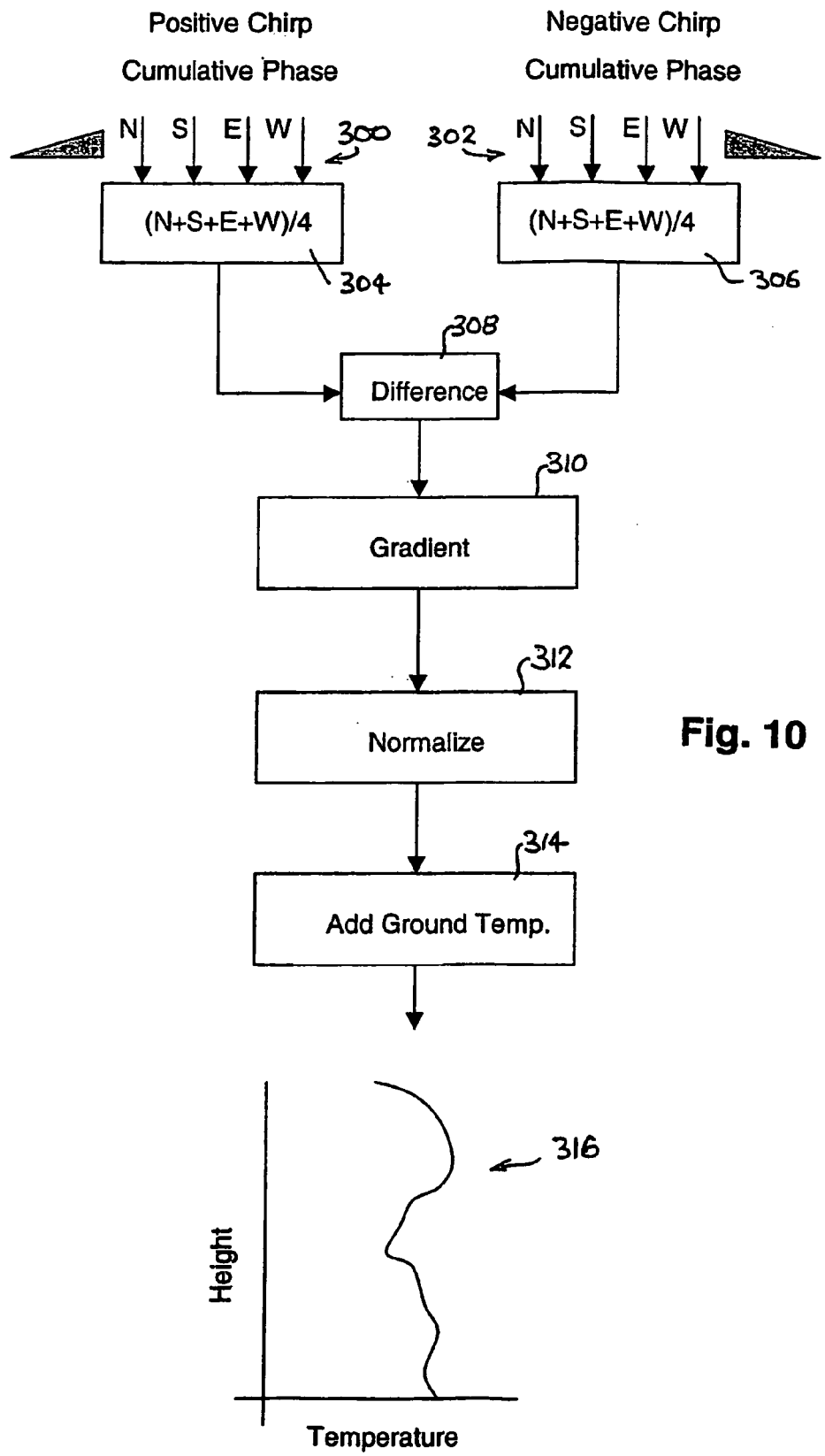
FIG. 10 is a block diagram illustrating portion of the process by which temperature with respect to height is derived
Figure 11:
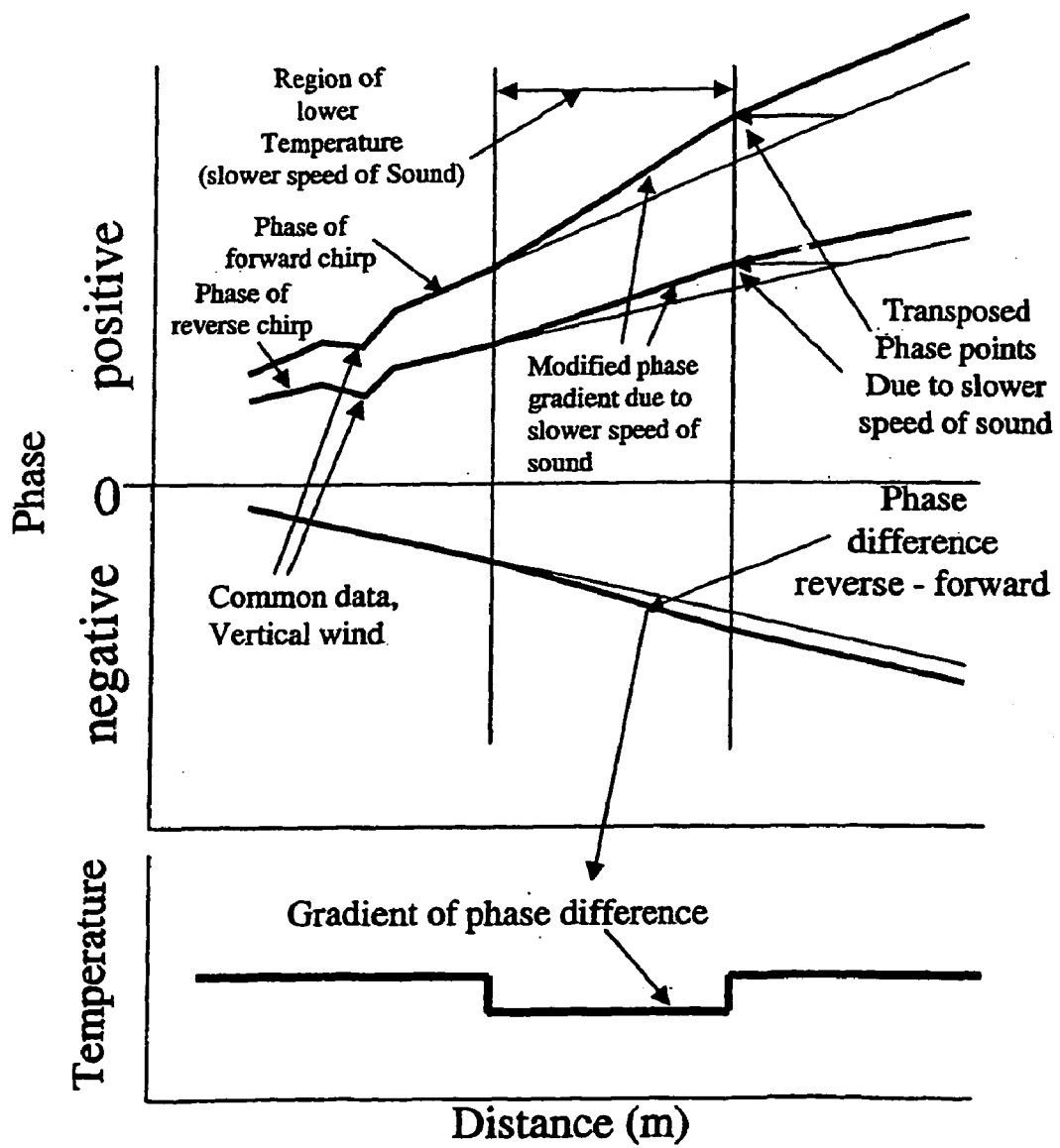
FIG. 11 is a graphical representation of how phase signals of positive and negative chirps are differenced to yield an indication of temperature with respect to range distance.
Figure 12:
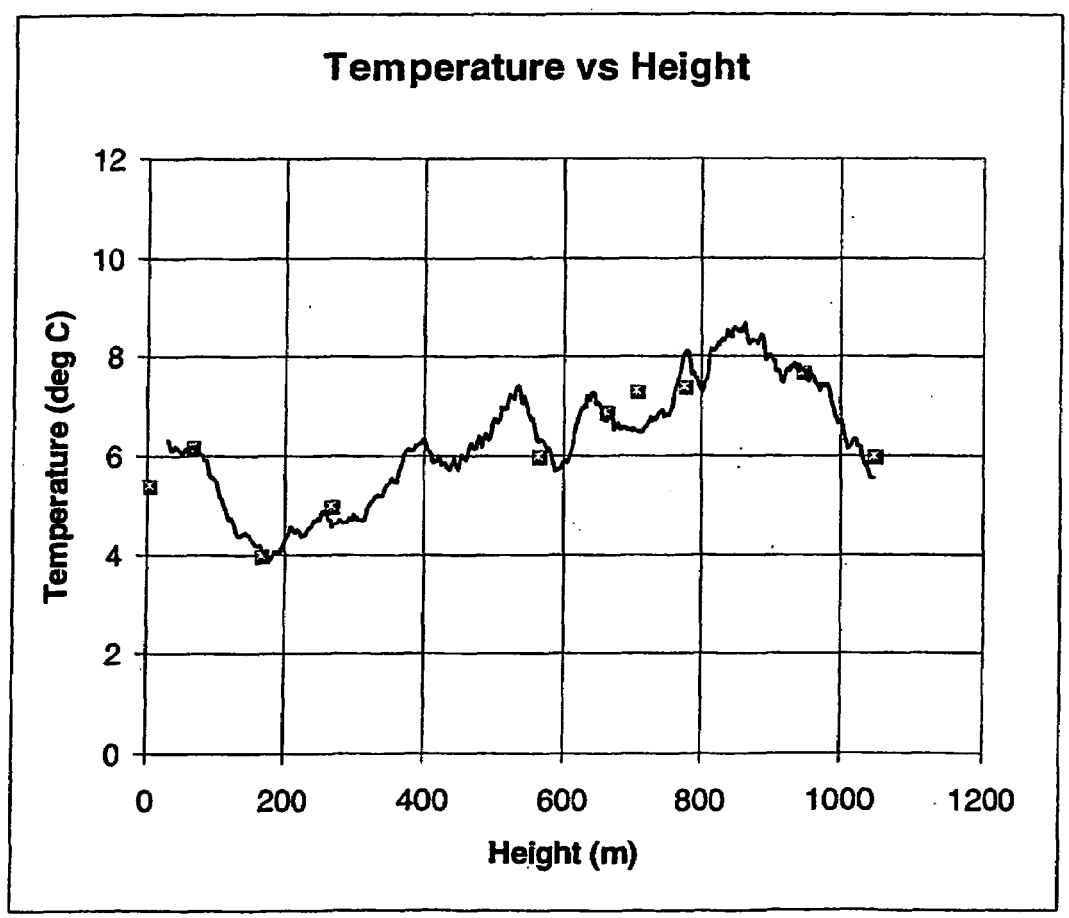
FIG. 12 is a plot of temperature with respect to range distance generated by the use of the disclosed system.

The manner in which the cumulative phase signals are manipulated will now be described with reference to FIG. 10, in which the N, S, E & W cumulative phase signals for the positive chirp are shown as inputs 300 and the N, S, E & W cumulative phase signals for the negative chirp are shown as inputs 302. Inputs 300 are added together and divided by four in adder 304 to remove the horizontal (cross-range) wind components for the positive chirp, and inputs 302 are added together and divided by four in adder 306 to remove the horizontal (cross-range) wind components for the negative chirp. The use of four receivers for temperature measurement is convenient as the same system can be used for horizontal wind measurements as well. The temperature measurement can also be made by using a single receiver pointed vertically but such a system could not be used for horizontal wind measurements. The outputs of adders 304 and 306 are then differenced in process 308 to remove common components due to direct signal, vertical wind, ground clutter and noise, leaving temperature related cumulative phase difference. The gradient of this difference signal is then derived in process 310 and normalized in process 312, the output of this process being a measure of the relative change of temperature with altitude (range). To calibrate this, the actual temperature near ground level is input at 314 and a chart—indicated at 316—of temperature variation with altitude can be generated. An actual chart generated by the means of the second example is appended as Figure The physical basis of temperature measurement in the system of this example is that the total rate of phase advance with respect to distance of a positive chirp passing through a layer of cold air will be slightly less than that for a negative chirp, the difference being dependent upon temperature. The total rate of phase advance is made up of the sum of a dominant component due to the propagation of sound in air (nominally 14,500$\pi$ radians for a distance of 1 km) and a minor component due to the internal rate of phase advance within the chirp (eg, +800×2$\pi$/43 or 18 radians/s for a positive chirp and −800×2$\pi$/43 or 18 radians/s for a negative chirp). In the case of a positive chirp, the internal rate is positive and is added to the propagation rate; with a negative chip the internal rate is negative and is subtracted from the propagation rate. Thus, the rate of increase of cumulative phase with respect to distance is slightly less for the negative chirp than for the positive chirp. However, when a cold layer of a fixed distance is encountered, the propagation rate of the positive chirp is slowed slightly so that the chirp takes longer to travel the distance the internal phase advance is proportionately greater than it was when traveling the same distance in warmer air. And, since the increased internal phase advance is positive, it will add slightly to the (now slower) propagational phase advance. While the cold layer also slows the propagation (phase rate) of the negative chirp and the internal (negative) phase advance is also increased as a result, the marginal increase is not as great due to the slower phase advance of the negative chirp and therefore results in a smaller total cumulative rate of phase change, resulting in a divergence of the rate of phase change with respect to time/distance. This is illustrated in the diagram of FIG. 11.

Measurement of Down-Range Wind Velocity

There are two ways of estimating down-range (in this case vertical) wind in accordance with the principles disclosed herein. The first (comprising the third example) is to use the central receiver 116 in a send-then-listen mode; the second (comprising the fourth example) is to use the four N, S, E & W receivers in a listen-while-sending mode. In both cases, long chirps (greater than 300 ms) are employed as taught herein but, in the first, there is some sacrifice of low-altitude range and, in the second, there is some sacrifice of accuracy.

In the third example, a short chirp of about 0.5 s is sent by loudspeaker 110 and, immediately after, the incoming signals to microphone 116 are processed by the phase and amplitude extraction process described above to generate an corresponding cumulative phase and amplitude output, from which vertical wind speed variation can be read or deduced. This method will lose the first 85 m of range and will be subject to errors due to noise and cross-range wind speed, but the greater resolution offered by the long chirp will be gained.

Figure 13:
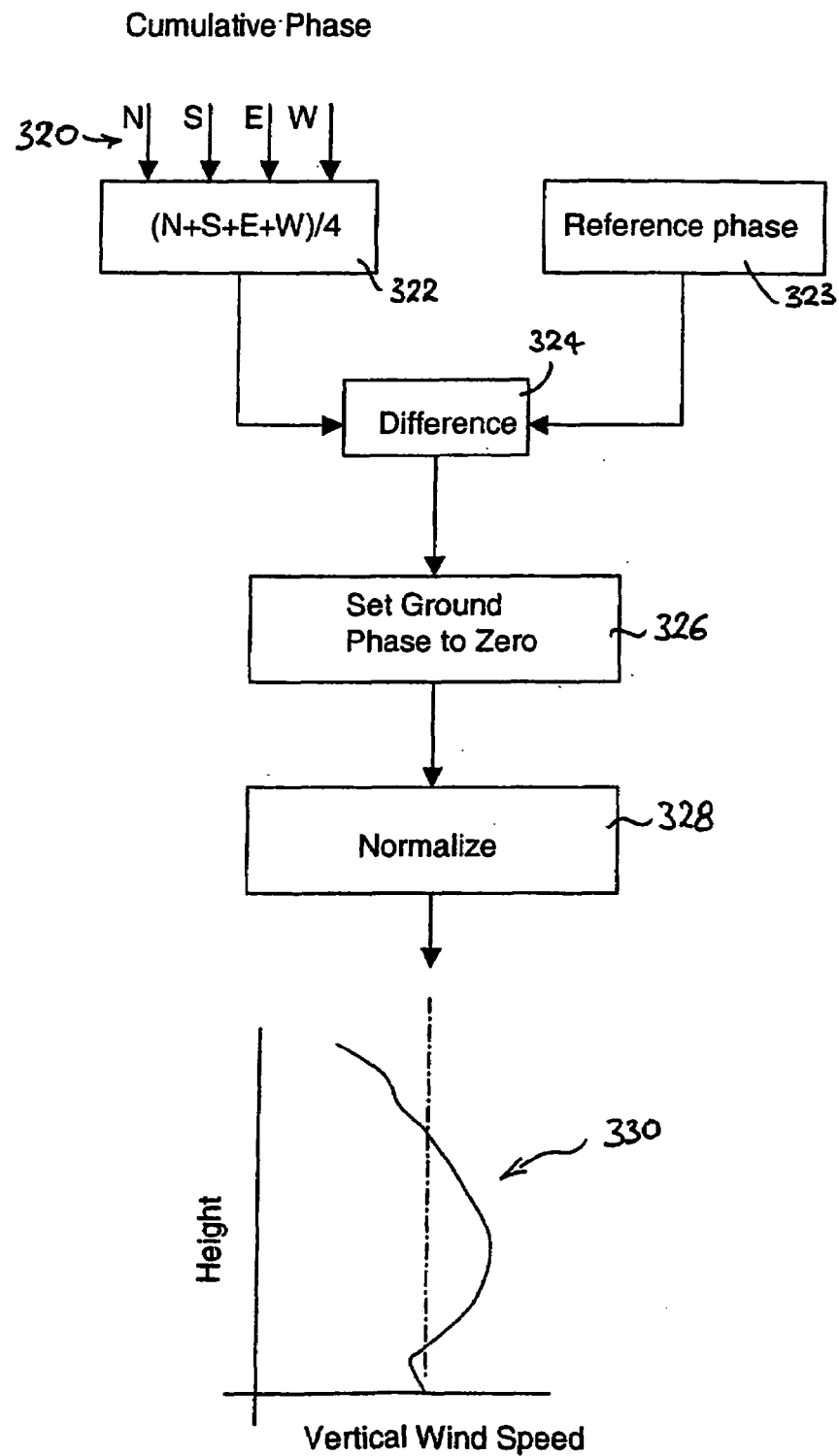
FIG. 13 is a block diagram illustrating portion of the process by which vertical wind speed with respect to height is derived.

In the fourth example, a chirp of about 5 s can be employed while all receivers are listening, the acoustic outputs of each receiver then being processed and the respective phases and amplitudes extracted as described above. Referring to FIG. 13, the cumulative phases of the N, S, E & W receivers, indicated at 320, are fed to adder 322 where they are added together and divided by four, as in the temperature measurement case to remove common elements due to cross-range wind. System dependent phase shift 323 is then removed in process 324, it being easily removed because it has a constant gradient. The output of process 324 is indicative of the variation of down-range wind speed, but is degraded by the (relatively short) direct signal and by ground clutter. These undesired signal components are manifest in a relatively large phase signal at the origin (zero distance and time) Since it is reasonable to assume that the wind speed at ground level is zero the initial or residual phase can be subtracted from the cumulative phase in process 326 and normalized in process 328, yielding the display indicated at 330. Alternatively, the resultant phase can be scaled and calibrated according to a known wind speed at a given altitude obtained by other means, such as radio sonde.

Detection of Vortices Near Runways

Figure 14:
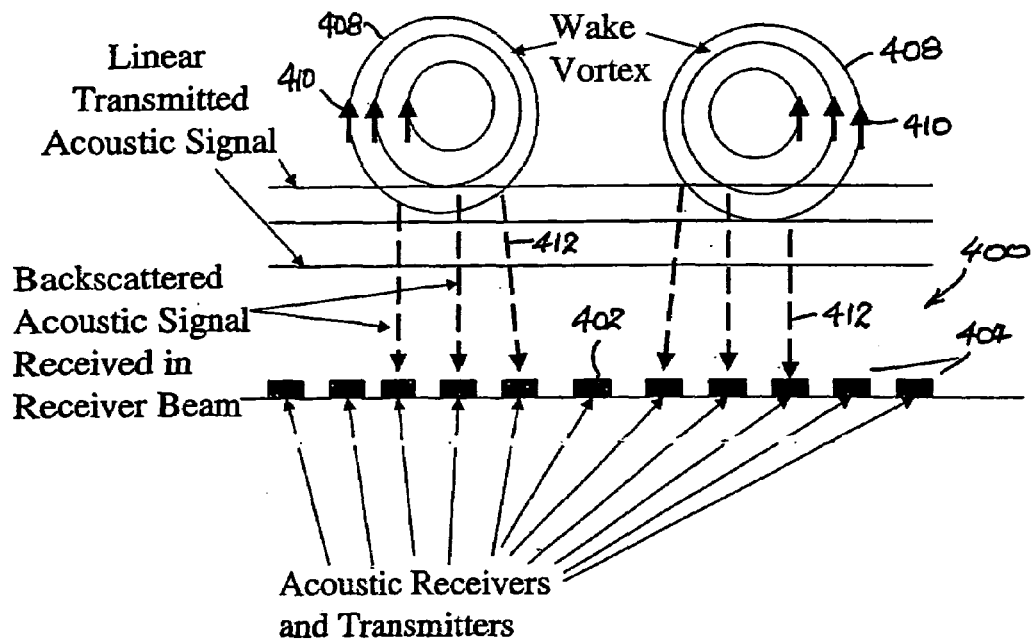
FIG. 14 is a schematic diagram illustrating the detection of wake vortices left by a large airplane near a runway.

In this fourth and final example, an array 400 of receivers and transmitters—such as indicated in FIG. 1(h) or (i)—is arranged across the glide path at the end of an airport runway. FIG. 14 shows the use of an array of the type shown in FIG. 1(h) having a single central transmitter 402 and multiple receivers 404 extending in a row on each side. The entire array may span 150-200 m. In FIG. 14 transmitter 402 is shown generating a spherically propagated acoustic chirp 406 and the wake vortices are shown at 408, arrows 410 indicating the direction of rotation of each vortex. The interaction of chirp 406 with the vortices results in the backscatter of echoes 412, which are picked up by receivers 404 and fed to respective matched filters in a manner similar to that described in the first example. Multiple receivers are used here to provide better horizontal resolution and increase overall receiver gain.

The difficulty in this case is, however, that the high Doppler echoes returned from the vortices creates considerable ambiguity in the results so that the location, size and speed of the vortices cannot be measured with sufficient accuracy by using the system of the first example alone. It is necessary to obtain measurements of the ambient conditions prior to the arrival of a large plane and use those measurements to adjust and sharpen those taken with a vortex present, after the plane has passed. The ambient measurement provides a reference for the amplitude and phase of the system as well as for the ambient amplitude and phase. These results are stored.

Figure 15:
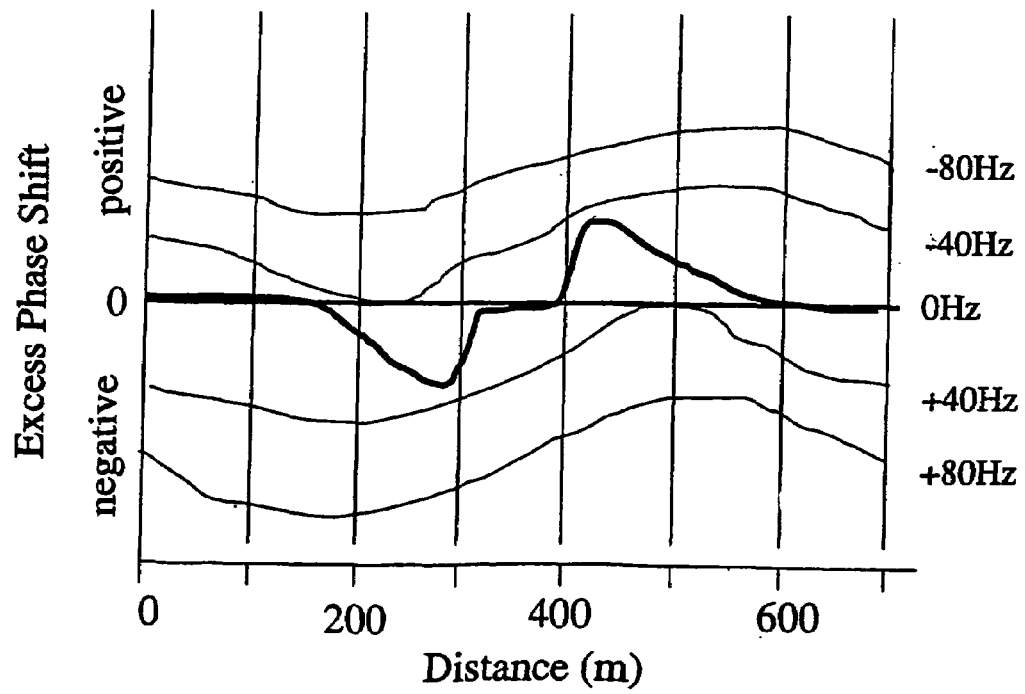
FIG. 15 is a graph showing the notional variation of excess phase with respect to range distance, this relationship being used to compute wind velocity and height in awake vortex.

When the echoes from a vortex are being processed, the signal processing proceeds for each receiver as described in the first example, except that the return signal is correlated against multiple different Doppler shifts (positive, zero and negative) for the internal multiply of the matched filter using a corresponding series of reference chirps generated by the control PC. Each phase calculated in respect of the vortex condition for each receiver is then differenced with the corresponding calculated phase for the ambient condition for each respective receiver, removing system and noise phase shifts. This leaves a residual or 'excess' phase shift that can be plotted with respect to distance (time) along with the corresponding Doppler shifts, as shown in FIG. 15.

To then estimate Doppler vs. distance (height), it is necessary to search through each excess phase record for each Doppler shifted result to find the distance ranges for which the excess phase is zero. By combining the ranges for which a zero excess phase is found a graph of Doppler shift vs. distance can be made. From this it is an easy matter to estimate wind speed vs. distance. It is to be noted that the excess phase alone cannot be used to without the additional Doppler processing because the range ambiguity effect spreads the excess phase result out to the extent that the location and size of the vortex cannot be sufficiently located.

Bradley (cited above) discusses a similar estimation process for the optimization of amplitude and reference should be made to that paper. However, using phase is more accurate and stable than amplitude, allowing a better estimation of Doppler to be obtained.

While some examples of the application of the invention have been described, it will be appreciated that the methods of the present invention can be applied widely to acoustic sounding and that many alterations and additions can be made without departing from the scope of the invention as defined by the following claims.

I claim:

1. A method for acoustically sounding air over a range that extends away from an acoustic transmitter and receiver the method comprising the steps of:
   transmitting an acoustic chirp comprising coded pulses having pulse compression waveforms and having a duration of at least 300 ms down-range,
   using the receiver to detect acoustic inputs and to generate a receiver output that is representative of said inputs, and
   processing said receiver output to generate signal phase data indicative of air characteristics in the range.

2. A method according to claim 1, wherein said step of using the receiver to detect acoustic inputs includes detecting echoes returned by the chirp while the chirp is still being transmitted.

3. A method according to claim 1 including the steps of:
   using the receiver means to detect first acoustic inputs, including echoes returned in a first direction from the chirp, to generate a first receiver output related to said first inputs,
   using the receiver means to detect second acoustic inputs, including echoes returned in a second direction from the chirp, to generate a second receiver output related to said second inputs,
   generating, using at least one of Fourier and matched filter techniques, a first phase signal comprising phase-related components from said first receiver output,
   generating, using at least one of Fourier and matched filter techniques, a second phase signal comprising phase-related components from said second receiver output,
   manipulation of said first and second phase signals to generate data relating air characteristics in range.

4. A method according to claim 3 wherein said manipulation includes the step of:
   adding said first and second phase signals to generate a first additive phase signal that emphasizes common components of said first and second phase signals indicative of down range air movement and to reduce components of said phase signals indicative of cross-range air movement.

5. A method according to claim 4 wherein said manipulation includes the step of:
subtracting from said first additive phase signal a reference phase signal indicative of system phase noise.

6. A method according to claim 3 wherein:
said first acoustic inputs include a first direct-chirp signal received direct from the transmitter having substantially no echo component,
said second acoustic inputs include a second direct-chirp signal received direct from the transmitter having substantially no echo component, and
said manipulation includes subtracting said first and second phase signals to generate a phase output signal that is substantially free of said first and second direct-chirp signals.

7. A method according to claim 3 wherein said manipulation includes:
removing phase signal components that are common to said first and second phase signals and that are at least in part due to system noise and to acoustic noise that is common to said first and second acoustic signals.

8. A method according to claim 3 wherein:
said first and second directions are inclined substantially equally and oppositely to one another and fall substantially in a first plane that extends cross-range, and
said manipulation of the first and second phase signals generates data indicative of cross-range air movement within or parallel to said first plane.

9. A method according to claim 3 including the steps of:
using the receiver to detect third acoustic inputs, including echoes returned in a third direction from the transmitted chirp, to generate a third receiver output related to said third inputs,
using the receiver to detect fourth acoustic inputs, including echoes returned in a fourth direction from the chirp, to generate a fourth receiver output related to said fourth inputs,
generating, using at least one of Fourier and matched filter techniques, a third phase signal comprising phase-related components from said third receiver output,
generating, using Fourier techniques, a fourth phase signal comprising phase-related components from said fourth receiver output, and
manipulation of said third and fourth phase signals to generate data relating air characteristics in range.

10. A method according to claim 9 wherein:
said third and fourth directions are inclined substantially equally and oppositely to one another and fall substantially in a second plane that extends cross-range, and
said manipulation of the third and fourth phase signals generates data indicative of cross-range air movement in said second plane, and
said manipulation of the third and fourth phase signals generates data indicative of cross-range air movement within or parallel to said second plane.

11. A method according to claim 10, wherein said first plane and said second planes are substantially orthogonal to one another, and said manipulation including the steps of:
differencing said first and second phase signals to remove phase signals common thereto and to generate first differential phase components indicative of air movement in or parallel to said first plane,
differencing said third and fourth phase signals to remove phase signals common thereto and to generate second differential phase components indicative of air movement in or parallel to said second plane.

12. A method according to claim 11 wherein said manipulation includes the step of combining the first and second differential phase signals to generate phase signals indicative of at least one of the bearing of cross-range wind relative to the down-range direction and phase signals indicative of cross-range wind shear.

13. A method according to claim 11 wherein:
the range extends substantially vertically from the transmitter and receiver means, which are located near at or near the base of the range,
the first and second planes are substantially vertical,
the first plane extends cross-range in a north-south alignment,
the second plane extends cross-range in an east-west alignment, and
said manipulation of said first, second third and fourth phase signals generates data indicative of the variation of the compass bearing and velocity of cross-range air movement.

14. A method according to claim 9 wherein said manipulation includes the step of:
adding said first, second, third and fourth phase signals to generate a second first additive phase signal that emphasizes common components of said first, second third and fourth phase signals indicative of down range air movement and to reduce components of said phase signals indicative of cross-range air movements.

15. A method according to claim 14 wherein said manipulation includes the step of:
subtracting from said second additive phase signal a reference phase signal indicative of system phase noise.

16. A method according to claim 1 wherein the chirp is a positive or negative linear acoustic signal that has an increasing or decreasing phase or frequency, or wherein both positive and negative linear chirps are employed.

17. A method according to claim 16 including the steps of:
transmitting positive and negative chirps in sequence,
deriving respective positive and negative versions of said receiver outputs,
processing said positive and negative receiver outputs to generate corresponding positive and negative signal phase data,
differencing said positive and negative signal phase data to generate third differential data indicative of variation of air temperature with range distance.

18. A method according to claim 16 including the steps of:
simultaneously transmitting positive and negative chirps that do not employ the same acoustic tones,
deriving respective positive and negative versions of said receiver outputs,
processing said positive and negative receiver outputs to generate corresponding positive and negative signal phase data,
differencing said positive and negative signal phase data to generate fourth differential data indicative of variation of air temperature with range distance.

19. A method according to claim 17 including the step of:
differentiating said respective third or fourth differential phase signal to derive a gradient signal that is indicative of the variation of air temperature with range distance.

20. A method according to claim 1
wherein said processing step includes generating ambient signal phase data in the absence of an air disturbance at a location, and including the steps of:
generating disturbance signal phase data in the presence of the local air disturbance at said location, and using said ambient signal phase data to normalize the disturbance signal phase data and to thereby generate normalized signal phase data.

21. A method according to claim 20 including the steps of:
correlating successive samples of said normalized phase data against multiple Doppler values to generate data indicative of wind speed with respect to distance.

22. A method according to claim 1 wherein signal amplitude data is generated and used together with said signal phase data.

23. A method according to claim 1 wherein the duration of the chirp is greater than five seconds.

24. A system for acoustically sounding air over a range that extends away from an acoustic transmitter and receiver comprising:
a transmitter adapted to transmit an acoustic chirp comprising coded pulses having pulse compression waveforms and having a duration of at least 300 ms down a range that extends away from the transmitter,
a receiver located near said transmitter and adapted to detect acoustic signals including echoes of the transmitted chirp returned from down-range and adapted to generate a receiver output that is representative of said received acoustic signals, and
a digital signal processor for processing said receiver output to generate signal phase data indicative of air characteristics in the range.

25. A system according to claim 24 wherein:
said receiver is adapted to detect a direct non-echo signal from the transmitter while it is transmitting, said direct signal contributing to said receiver output.

26. A system according to claim 24 wherein:
said receiver is adapted to detect first acoustic inputs, including echoes returned in a first direction from the chirp, and to generate a first receiver output related to said first inputs,
said receiver is adapted to detect second acoustic inputs, including echoes returned in a second direction from the chirp, and to generate a second receiver output related to said second inputs,
said signal processor is adapted to
receive said first and second receiver outputs,
process said outputs using at least one of a matched filter and a Fourier processor,
generate respective first and second phase signals, and manipulate said first and second phase signals to generate data relating air characteristics in the range.

27. A system according to claim 26 wherein the signal processor, when manipulating said first and second phase signals, is adapted to:
add said first and second phase signals to generate a first additive phase signal that emphasizes common components of said first and second phase signals indicative of down range air movement and to reduce components of said phase signals indicative of cross-range air movement.

28. A system according to claim 27 wherein the signal processor, when manipulating said first and second phase signals, is adapted to:
subtract from said first additive phase signal a reference phase signal indicative of system phase noise.

29. A system according to claim 26 wherein the signal processor, when manipulating said first and second phase signals, is adapted to:
subtract said first and second phase signals to generate a phase output signal that is substantially free of direct-chirp signal components.

30. A system according to claim 26 wherein the signal processor, when manipulating said first and second phase signals, is adapted to:
remove phase signal components that are common to said first and second phase signals and that are inter alia due to system noise and to acoustic noise that is common to said first and second acoustic signals.

31. A system according to claim 26 wherein:
said first and second directions are inclined substantially equally and oppositely to one another and fall substantially in a first plane that extends cross-range, and
the signal processor, when manipulating said first and second phase signals, is adapted to generate data indicative of cross-range air movement within or parallel to said first plane.

32. A system according to claim 26 wherein:
said receiver is adapted to detect third acoustic inputs, including echoes returned in a third direction from the transmitted chirp, to generate a third receiver output related to said third inputs,
said receiver is adapted to detect fourth acoustic inputs, including echoes returned in a fourth direction from the chirp, to generate a fourth receiver output related to said fourth inputs,
said signal processor is adapted to use at least one of Fourier and matched filter techniques to generate a third phase signal comprising phase-related components from said third receiver output,
said signal processor is adapted to use at least one of Fourier and matched filter techniques to generate a fourth phase signal comprising phase-related components from said fourth receiver output, and
said signal processor is adapted to manipulate said third and fourth phase signals to generate data relating air characteristics in the range.

33. A system according to claim 32 wherein:
said third and fourth directions are inclined substantially equally and oppositely to one another and fall substantially in a second plane that extends cross-range, and
said manipulation of the third and fourth phase signals is adapted to generate data indicative of cross-range air movement in said second plane, and
said signal processor is adapted to manipulate the third and fourth phase signals to generate data indicative of cross-range air movement within or parallel to said second plane.

34. A system according to claim 33, wherein said first plane and said second planes are substantially orthogonal to one another, and wherein:
said signal processor is adapted to:
difference said first and second phase signals to remove phase signals common thereto and to generate first differential phase components indicative of air movement in or parallel to said first plane, and
difference said third and fourth phase signals to remove phase signals common thereto and to generate second differential phase components indicative of air movement in or parallel to said second plane.

35. A system according to claim 34 wherein said signal processor is adapted to combine the first and second differential phase signals to generate phase signals indicative of the bearing of cross-range wind relative to at least one of the downrange direction and phase signals indicative of cross-range wind shear.

36. A system according to claim 34 wherein:
the range extends substantially vertically from the transmitter and receiver, which are adapted to be located at or near the base of the range,
the first and second planes are substantially vertical,
the first plane extends cross-range in a north-south alignment,
the second plane extends cross-range in an east-west alignment, and said signal processor is adapted to manipulate said first, second third and fourth phase signals to generate data indicative of the variation of the compass bearing and velocity of cross-range air movement.

37. A system according to claim 33 wherein said signal processor is adapted to add said first, second, third and fourth phase signals to generate a second first additive phase signal that emphasizes common components of said first, second, third and fourth phase signals indicative of down range air movement and to reduce components of said phase signals indicative of cross-range air movements.

38. A system according to claim 36 wherein said signal processor is adapted to subtract from said second additive phase signal a reference phase signal indicative of system phase noise.

39. A system according to claim 24 wherein the transmitter is adapted to transmit a chirp comprising a positive or negative linear acoustic signal that has an increasing or decreasing phase or frequency, or wherein both positive and negative linear chirp's are employed.

40. A system according to claim 39 wherein:
the transmitter is adapted to transmit positive and negative chirps in sequence,
the receiver is adapted to generate respective positive and negative versions of said receiver outputs from acoustic input signals including said positive and negative chirps and echoes thereof,
said signal processor is adapted to:
process said positive and negative receiver outputs to generate corresponding positive and negative signal phase data, and
difference said positive and negative signal phase data to generate third differential data indicative of variation of air temperature with range distance.

41. A system according to claim 39 wherein:
said transmitter is adapted to simultaneously transmit positive and negative chirps that do not employ the same acoustic tones,
said receiver is adapted to generate respective positive and negative receiver outputs,
said signal processor is adapted to:
process said positive and negative receiver outputs to generate corresponding positive and negative signal phase data, and
difference said positive and negative signal phase data to generate fourth differential data indicative of variation of air temperature with range distance.

42. A system according to claim 40 wherein:
said signal processor is adapted to differentiate said (respective) third or fourth differential phase signal to derive a gradient signal that is indicative of the variation of air temperature with range distance.

43. A system according to claim 24 adapted to:
generate ambient signal phase data in the manner claimed in the absence of an air disturbance at a location,
generate disturbance signal phase data in the presence of the local air disturbance at said location, and
use said ambient signal phase data to normalize the disturbance signal phase data and to thereby generate normalized signal phase data.

44. A system according to claim 43 wherein said signal processor is adapted to correlate successive samples of said normalized phase data against multiple Doppler values to generate data indicative of wind speed with respect to distance.

* * * * *